United States Patent [19]

Ito et al.

[11] Patent Number: 5,859,011

[45] Date of Patent: Jan. 12, 1999

[54] DIHYDROPYRIDINE DERIVATIVES AS BRADYKININ ANTAGONIST

[75] Inventors: Fumitaka Ito, Aichi; Hiroshi Kondo, Handa, both of Japan; David L. Hageman, Colchester; John A. Lowe, III, Stonington, both of Conn.; Susumu Nakanishi, Tacoma, Wash.; Fredric J. Vinick, Winchester, Mass.

[73] Assignee: Pfizer Inc., New York, N.Y.

[21] Appl. No.: 793,561

[22] PCT Filed: May 26, 1995

[86] PCT No.: PCT/IB95/00400

§ 371 Date: Jul. 1, 1997

§ 102(e) Date: Jul. 1, 1997

[87] PCT Pub. No.: WO96/06082

PCT Pub. Date: Feb. 29, 1996

[30] Foreign Application Priority Data

Aug. 24, 1994 [WO]  WIPO ........................ PCT/JP94/01398

[51] Int. Cl.⁶ .......................... C07D 401/06; A61K 31/50
[52] U.S. Cl. .......................... 514/252; 514/255; 514/256; 544/365; 544/362; 544/333
[58] Field of Search ..................... 544/365, 362, 544/333; 514/252, 255, 256

[56] References Cited

U.S. PATENT DOCUMENTS 5,120,750  6/1992  Daneshtalab et al. ................... 514/370
5,162,497  11/1992  Coy et al. ................. 530/314
5,610,142  3/1997  Mavunkel et al. ......................... 514/16

OTHER PUBLICATIONS

Principles pf psychopharmacology Academic Press, Clark et al. p. 166, 1970.

Primary Examiner—Jane Fan
Attorney, Agent, or Firm—Peter C. Richardson; Paul H. Ginsburg

[57] ABSTRACT

Compound of formula (1) and their pharmaceutically acceptable salts wherein A1,A2,R1, R2,R3,R4,X are as defined in the specification have excellent bradykinin antagonistic activity.

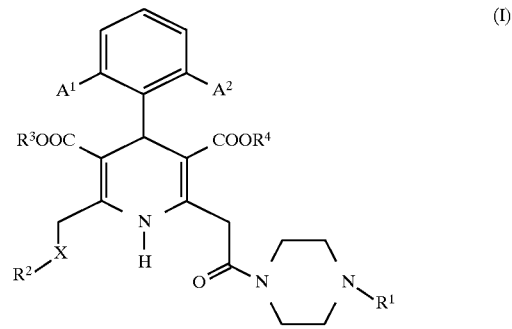

13 Claims, No Drawings

DIHYDROPYRIDINE DERIVATIVES AS BRADYKININ ANTAGONIST

This application is a 371 of PCT/IB95/00400 filed May 26, 1995.

TECHNICAL FIELD

This invention relates to novel 1,4-dihydropyridine compounds, and more particularly to 1,4-dihydropyridine compounds having a substituted or unsubstituted-piperazinylcarbonylmethyl group attached to the 2-position of the dihydropyridine ring. These compounds are useful as antagonists of bradykinin, and are thus useful in the treatment of inflammation, cardiovascular disease, pain, common cold, allergies, asthma, pancreatitis, burns, virus infection, head injury, multiple trauma or the like in mammalia, especially humans. The present invention also relates to a pharmaceutical composition useful in the treatment of the above clinical conditions, which comprises the 1,4-dihydropyridine compound of the invention and a pharmaceutically acceptable carrier.

BACKGROUND ART

Bradykinin ("BK") is generated under normal conditions in mammalia by the action of various plasma enzymes such as kallikrein on high molecular weight kininogens. It is widely distributed in mammals, as are its two receptor subtypes, $BK_1$ and $BK_2$. The actions of BK at the BK1 receptor include mainly contraction of arterial and venous preparations, although it can cause relaxation of peripheral resistance vessels as well.

Many of the more important functions of BK, as increases in vascular permeability, pain, and vasodilatation, however, are mediated by the BK2 receptor. These effects at the $BK_2$ receptor are believed to be responsible for BK's role in numerous diseases, such as inflammation, cardiovascular disease, pain, and the common cold. Hence antagonists at the $BK_2$ receptor should find considerable therapeutic applications. Most of the efforts in this area thus far have been directed at peptidic analogues of the BK structure, some of which have been studied as analgesics and antiinflammatory agents.

It would be desirable if there were provided a non-peptide antagonist of the $BK_2$ receptor, having a good $BK_2$ antagonistic activity and a good metabolic stability. A variety of dihydropyridine compounds have been synthesized in the field of antihypertensive agents. However, none of these dihydropyridine compounds have been reported as bradykinin antagonists.

BRIEF DISCLOSURE OF THE INVENTION

The present invention provides a compound of the formula:

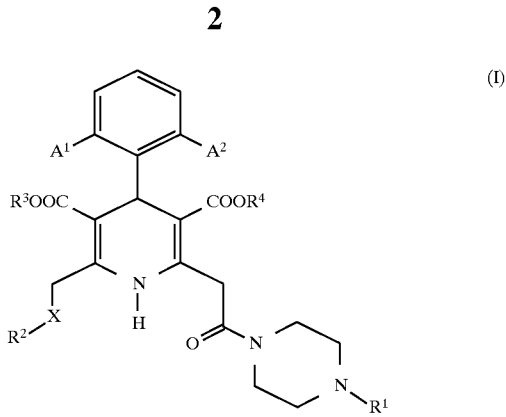

and its pharmaceutically acceptable salts, wherein
$A^1$ and $A^2$ are each halo;
X is a direct bond, $CH_2$, CO, O, S, S(O) or $S(O)_2$;
$R^1$ is selected from the following:
(a) hydrogen, $C_{1-4}$ alkyl optionally substituted with one or two substituents selected from hydroxy, amino, $C_{1-4}$ alkylamino, di-$C_{1-4}$ alkylamino, pyridyl, carbamoyl, pyrrolidinocarbonyl, propylaminocarbonyl, piperidinocarbonyl or morpholinocarbonyl;
(b) piperidinyl optionally substituted on the nitrogen atom with $C_{1-4}$ alkyl or $C_{1-4}$ alkoxycarbonyl;
(c) $C_{5-14}$ cycloalkyl, bicycloalkyl or tricycloalkyl, optionally substituted with one or two substituents selected from oxo, hydroxy, amino, $C_{1-4}$ alkylamino, di-$C_{1-4}$ alkylamino, methoxybenzamido or morpholino;
(d) $C_{7-14}$ azacyclo-, azabicyclo- or azatricyclo-alkyl, in which the nitrogen atom optionally has a substituent selected from $C_{1-4}$ alkyl, benzyl optionally substituted with one or two substituents selected from halo and trihalo $C_{1-4}$ alkyl, $C_{1-4}$ alkyloxycarbonyl optionally substituted with one or two halogen atoms and $C_{2-5}$ acyl; and
(e) $C_{7-10}$ bicycloalkenyl, benzo $C_{5-7}$ cycloalkyl or heterocyclic as herinafter defined;
$R^2$ is hydrogen, $C_{1-4}$ alkyl, phenyl optionally substituted with one or two substituents selected from halo, $C_{1-4}$ alkyl, trihalo $C_{1-4}$ alkyl and $C_{1-4}$ alkoxy, or heterocyclic as herinafter defined; and
$R^3$ and $R^4$ are each $C_{1-5}$ alkyl.

The dihydropyridine compounds of this invention have excellent bradykinin antagonistic activity and are thus useful for the treatment of inflammation, cardiovascular diseas, pain, common cold, allergies, asthma, pancreatitis, burns, virus infection, head injury, multiple trauma or the like in mammalia, especially humans.

The present invention also provides a pharmaceutical composition for the treatment of inflammation, cardiovascular disease, pain, common cold, allergies, asthma, pancreatitis, burns, virus infection, head injury, multiple trauma or the like, which comprises a therapeutically effective amount of the dihydropyridine compound of formula (I) or its pharmaceutically acceptable salt together with a pharmaceutically acceptable carrier.

DETAILED DESCRIPTION OF THE INVENTION

As used herein, the term "$C_{1-4}$ alkylamino" and "$C_{1-4}$ dialkylamino" mean N(R')R'', wherein R' is hydrogen or $C_{1-4}$ alkyl and R'' is $C_{1-4}$ alkyl, such as methylamino, ethylamino, n-propylamino, isopropylamino, n-butylamino, t-butylamino, dimethylamino, diethylamino and ethylmethylamino;

- the term "$C_{5-14}$ cycloalkyl, bicycloalkyl or tricycloalkyl" means monocyclic, bicyclic or tricyclic alkyl having 5 to 14 carbon atoms, such as cyclopentyl, cycloheptyl, cyclooctyl, bicyclo[3.2.1]octyl, bicyclo[3.3.0]octyl and tricyclo[4.3.3.0]dodecyl;
- the term "$C_{7-14}$ azacyclo-, azabicyclo- or azatricycloalkyl" means monocyclic, bicyclic or tricyclic alkyl having 7 to 14 carbon atoms and one nitrogen atom in the ring, such as azabicyclo[3.2.1]octyl, azabicyclo[3.3.1]nonyl, and azatricyclo[3.3.3.0]undecyl; and
- the term "heterocyclic" means a monocyclic or bicyclic hydrocarbon group which has one or more hetero atoms in the ring, preferably has 4 to 10 carbon atoms and 1 to 3 heteroatoms, including piperidino, morpholino, thiamorpholino, pyrrolidino, pyrazolino, pyrazolidino, pyrazoryl, piperazinyl, furyl, thienyl, oxazolyl, tetrazolyl, thiazolyl, imidazolyl, pyrazolyl, pyridyl, pyrimidinyl, pyrrolyl, pyrrolidinyl, quinolyl and quinuclidinyl.

In the above formula (I), $A^1$ and $A^2$ may be the same as or different from each other, and are selected from chloro, bromo, iodo and fluoro, preferably chloro and bromo.

In the above formula (I), X is preferably a direct bond or $CH_2$.

In the above formula (I), examples of $R^1$ selected from group (a) are hydrogen, pyridylmethyl, pyrrolidinylcarbonyl, propylaminocarbonyl, hydroxyethyl and dimethylaminopropyl.

Examples of $R^1$ selected from group (b) are piperidinyl, 1-(butylcarbonyl)piperidinyl and 1-methylpiperidinyl.

Examples of $R^1$ selected from group (c) are $C_{5-6}$ cycloalkyl, bicyclo[3.2.1]octyl and one of the following:

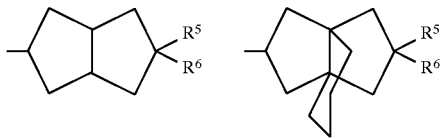

(wherein $R^5$ is hydrogen and $R^6$ is hydroxy, amino, methoxybenzamido or morpholino, or $R^5$ and $R^6$ are taken together to represent an oxo group).

Examples of $R^1$ selected from group (d) are the following groups:

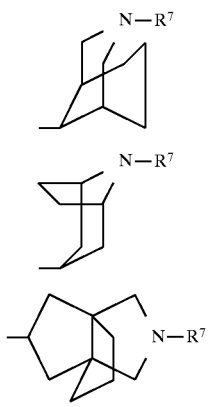

-continued

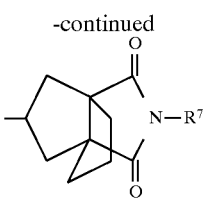

(wherein $R^7$ is hydrogen, $C_{1-4}$ alkyl, benzyl optionally substituted with one or two substituents selected from halo and trihaloalkyl, acetyl or chloroethoxycarbonyl).

Examples of $R^1$ selected from group (e) are norbornenyl, indanonyl, quinuclidinyl or pyrimidinyl.

In the above formula (I), examples of $R^2$ are hydrogen, phenyl, methoxyphenyl, propyl(methoxy)phenyl, methylphenyl, chlorophenyl, pyridyl and thienyl.

In the above formula (I), examples of $R^3$ and $R^4$ are methyl, ethyl, propyl, t-butyl, s-butyl and pentyl, preferably $C_{1-3}$ alkyl such as methyl and ethyl.

Among the dihydropyridine compounds of this invention, preferred individual compounds are:

dimethyl 4-(2,6-dichlorophenyl)-2-(4-methyl-1-piperazinyl)carbonylmethyl-6-phenylsulfinylmethyl-1,4-dihydropyridine-3,5-dicarboxylate;

dimethyl 4-(2,6-dichlorophenyl)-2-(4-methyl-1-piperazinyl)carbonylmethyl-6-(2-tolyl)sulfinylmethyl-1,4-dihydropyridine-3,5-dicarboxylate;

dimethyl 4-(2,6-dichlorophenyl)-2-(4-methyl-1-piperazinyl)carbonylmethyl-6-(2-pyridyl)sulfinylmethyl-1,4-dihydropyridine-3,5-dicarboxylate;

dimethyl 4-(2,6-dichlorophenyl)-6-[2-(2-methoxyphenyl)ethyl]-2-(4-pyrrolidinyl-carbonylmethyl-1-piperazinyl)carbonylmethyl-1,4-dihydropyridine-3,5-dicarboxylate;

dimethyl 4-(2,6-dichlorophenyl)-6-(2-phenylethyl)-2-(4-pyrrolidinylcarbonylmethyl-1-piperazinyl)carbonylmethyl-1,4-dihydropyridine-3,5-dicarboxylate;

dimethyl 4-(2,6-dichlorophenyl)-6-[2-(2-methoxyphenyl)ethyl]-2-[4-(1-methyl-4-piperidinyl)-1-piperazinyl]carbonylmethyl-1,4-dihydropyridine-3,5-dicarboxylate;

dimethyl 4-(2,6-dichlorophenyl)-6-[2-(2-methoxyphenyl)ethyl]-2-[4-(8-methyl-8-azabicyclo[3.2.1]octan-3-yl)-1-piperazinyl]carbonylmethyl-1,4-dihydropyridine-3,5-dicarboxylate;

dimethyl 4-(2,6-dichlorophenyl)-6-[2-(2-methoxyphenyl)ethyl]-2-[4-(3-quinuclidinyl)-1-piperazinyl]carbonylmethyl-1,4-dihydropyridine-3,5-dicarboxylate;

dimethyl 2-[4-(8-benzyl-8-azabicyclo[3.2.1]octan-3-yl)-1-piperazinyl]carbonylmethyl-4-(2,6-dichlorophenyl)-6-[2-(2-methoxyphenyl)ethyl]-1,4-dihydropyridine-3,5-dicarboxylate;

dimethyl 2-[4-(bicyclo[3.3.0]octan-3-one-7-yl)-1-piperazinyl]carbonylmetnyl-4-(2,6-dichlorophenyl)-6-[2-(2-methoxyphenyl)ethyl]-1,4-dihydropyridine-3,5-dicarboxylate;

dimethyl 2-[4-(bicyclo[3.3.0]octan-3-ol-7-yl)-1-piperazinyl]carbonylmethyl-4-(2,6-dichlorophenyl)-6-[2-(2-methoxyphenyl)ethyl]-1,4-dihydropyridine-3,5-dicarboxylate;

dimethyl 2-[4-(bicyclo[3.3.0]octan-3-amine-7-yl)-1-piperazinyl]carbonylmethyl4-(2,6-dichlorophenyl)-6-[2-(2-methoxyphenyl)ethyl]-1,4-dihydropyridine-3,5-dicarboxylate; and dimethyl 4-(2,6-dichlorophenyl)-2-(4-methyl-1-piperazinyl)carbonylmethyl-6-phenacyl-1,4-dihydropyridine-3,5-dicarboxylate.

Of these compounds, the most preferred compounds are:

dimethyl 4-(2,6-dichlorophenyl)-2-(4-methyl-1-piperazinyl)carbonylmethyl-6-phenylsulfinylmethyl-1,4-dihydropyridine-3,5-dicarboxylate;

dimethyl 4-(2,6-dichlorophenyl)-6-[2-(2-methoxyphenyl) ethyl]-2-[4-(8-methyl-8-azabicyclo[3.2.1 ]octan-3-yl)-1-piperazinyl]carbonylmethyl-1,4-dihydropyridine-3,5-dicarboxylate; and dimethyl 4-(2,6-dichlorophenyl)-6-[2-(2-methoxyphenyl) ethyl]-2-[4-(3-quinuclidinyl)-1-piperazinyl] carbonylmethyl-1,4-dihydropyridine-3,5-dicarboxylate.

The dihydropyridine compounds of formula (I) of this invention may be prepared by a variety of synthetic methods known to those skilled in the art. For example, the dihydropyridine compounds of formula (I) may be prepared by reaction of compound (II) with compound (III), followed, if desired, by conversion of a compound in which $R^1$ is H into a compound in which $R^1$ is other than H, as indicated in the following Preparation Method A.

Preparation Method A:

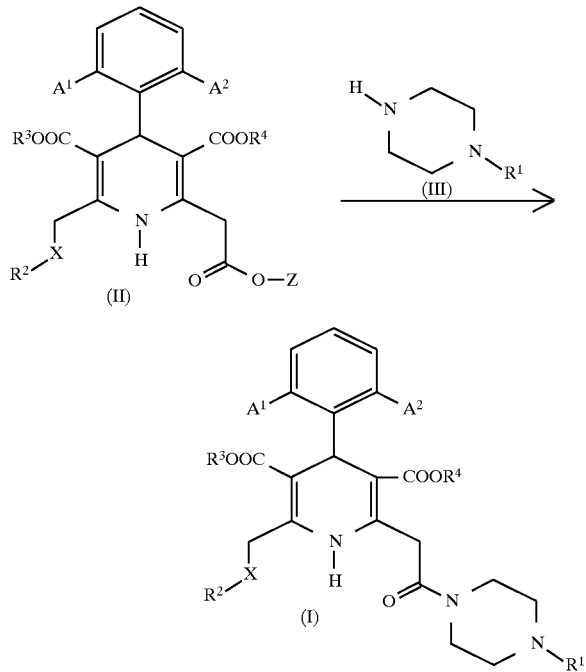

(wherein Z is hydrogen or lower alkyl such as methyl and ethyl; and the other symbols are as already defined)

In Preparation Method A, when Z is lower alkyl, the compound (II) may be first subjected to selective saponification of the ester residue at the 2-position of the compound (II), followed by acidification to afford a free acid, which is coupled with the piperazine compound (III) to give the dihydropyridine compounds (I). When Z is H, the compound (II) may be directly coupled with the piperazine compound (III) to obtain the dihydropyridine compounds (I).

The selective saponification and the acidification may be carried out by conventional procedures. In a typical procedure, the selective saponification is carried out by treatment with 6N sodium hydroxide in aqueous methanol. In a typical procedure, the acidification is carried out by treatment with 1N hydrochloric acid in a suitable reaction-inert solvent.

The coupling reaction between the obtained acid and piperazine (wherein $R^1$ is H) or 4-N-substituted piperazine (wherein $R^1$ is other than H) may be carried out in a reaction-inert solvent as listed above (preferably dichloromethane) using a coupling agent such as dicyclohexylcarbodiimide (DCC), water soluble carbodiimide (WSCD), 2-ethoxy-N-ethoxycarbonyl-1,2dihydroquinoline, Bop agent (Benzotriazol-1-yloxy-tris(dimethylamino) phosphonium hexafluorophosphate), diethyl azodicarboxylate-triphenylphosphine, diethylcyanophosphonic acid and diphenylphospholylazide. This reaction may be carried out at a temperature of 0° C. to 25° C. for 30 minutes to 20 hours.

A compound (I) wherein $R^1$ is other than H can be obtained from the corresponding compound (I) wherein $R^1$ is H, by reductive alkylation of the terminal nitrogen with appropriate aldehyde or ketone. The reductive alkylation may be carried out in a suitable reaction-inert solvent, in the presence of a suitable reducing agent such as $NaBH_4$, $NaBH_3CN$ or $NaBH(OAc)_3$ at a temperature of 0° to 80° C. for 30 minutes to 50 hours.

In addition, the 4-N-substituted piperazines (III) as used herein may be either known or may be prepared by known methods. For example, the 4-N-substituted piperazines may be prepared by means of (1) N alkylation of 4-N-protected piperazine with appropriate alkyl halide, $R^1$-halo, or (2) reductive amination of 4-N-protected piperazine with appropriate aldehyde or ketone in the presence of a reducing agent, followed by deprotection of the amino-protecting group. Suitable amino-protecting groups include, for example, benzyloxycarbonyl and t-butoxycarbonyl group. Suitable reducing agents include, for example, sodium cyanoborohydride, aluminum-based reducing reagents, boranes, borohydrides or trialkylsilanes. After finishing introduction of a desired R1 group, the amino-protecting group is removed by a suitable standard procedure to provide the objective compound.

The compound (II) may be prepared by several methods as indicated in the following Preparation Methods B-I to B-III.

Preparation Method B-I:

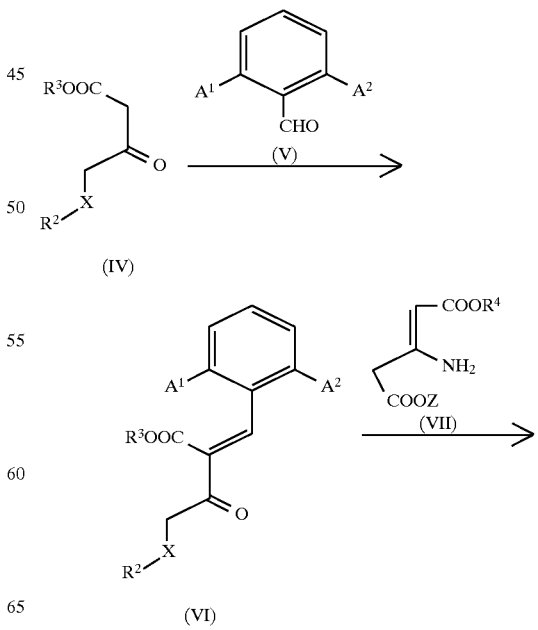

-continued

Preparation Method B-I:

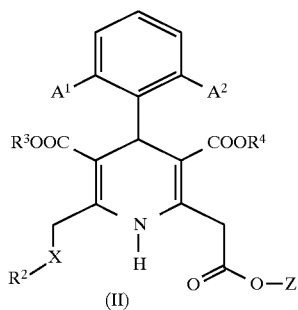

(II)

This method utilizes the modified Hantzsch synthesis as described in A. Sausins and G. Duburs, *Heterocycles*, 1988, 27, 269. In this method, beta-keto ester (IV) is first reacted with substituted benzaldehyde (V) to obtain Compound (VI). This reaction may be carried out in a suitable reaction-inert solvent. Suitable solvents include, for example, aromatic hydrocarbons such as benzene, toluene and xylene; alcohols such as methanol, ethanol, propanol and butanol; ethers such as ethyl ether, dioxane and tetrahydrofuran; halogenated hydrocarbons such as methylene chloride, chloroform and dichloroethane; amides such as N,N-dimethylformamide; and nitriles such as acetonitrile. This reaction may be carried out at a temperature of 0° C. to 200° C., preferably from 80° C. to 120° C. for 30 minutes to 24 hours, preferably 30 minutes to 6 hours. If desired, this reaction may be catalyzed by a base such as piperidine, pyridine or alkoxide, or by an acid catalyst such as acetic acid, $TiCl_4$ or p-toluenesulfonic acid.

Thereafter, Compound (VI) as obtained above is reacted with Compound (VII) in the presence of, or absence of a suitable condensing agent such as Lewis acids, to obtain the pyridine compound of the formula (II). This reaction may be carried out in the presence of, or absence of the reaction-inert solvent as listed above. However, this reaction may preferably carried out in the absence of a solvent. This reaction may be carried out at a temperature of 0° C. to 200° C., preferably, from 60° C. to 150° C. for 30 minutes to 48 hours, preferably 10 hours to 20 hours.

In addition, the beta-keto esters (IV) and the substituted benzaldehydes (V) which can be used herein may be either already known or may be-prepared by known methods. For example, the beta-keto esters (IV) may be prepared according to the reported methods as shown in, for example, (1) D. Scherling, *J. Labelled Compds. Radiopharm.*, 1989, 27, 599; (2) C. R. Holmquist and E. J. Roskamp, *J. Org. Chem.*, 1989, 54, 3258; (3) S. N. Huckin and L. Weiler, *J. Am. Chem. S°C.*, 1974, 96, 1082; (4) *J. C. S. Perkin I*, 1979, 529; and (5) *Synthesis*, 1986, 37; *J. C. S. Chem. Commun.*, 1977, 932).

Preparation Method B-II:

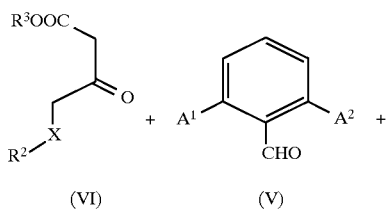

Preparation Method B-II:

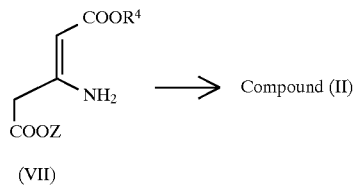

(VII)

(wherein all the symbols are as already defined)

This method utilizes the three components Hantzsch reaction. In a typical procedure, the beta-keto ester (IV), the substituted benzealdehyde (V) and Compound (VII) may be heated together in a suitable reaction-inert solvent as listed above (preferably lower alkanols such as methanol and ethanol). Preferably, a small amount of a lower alkanoic acid such as acetic acid is added as catalyst. The reaction mixture may be heated at 0° C. to 200° C., preferably from room temperature to refulx temperature for 30 minutes to 1 week.

Preparation Method B-III:

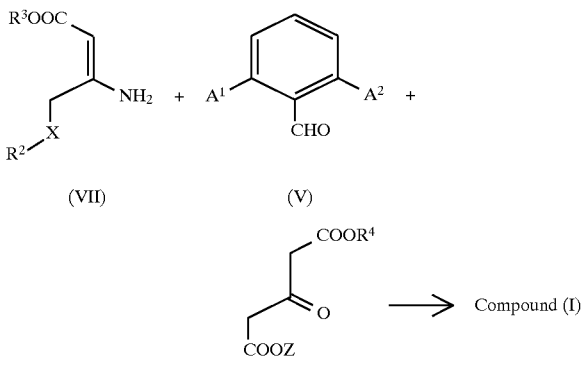

(wherein all the symbols are as already defined)

This method also utilizes the three components Hantzsch reaction as mentioned above. The reaction conditions similar to the above can be also used in this method.

The compound (VIII), enamine may either be known compounds or may be prepared by known methods. For example, the enamine compounds (VIII) may be prepared by reacting the beta-keto ester (IV) with ammonia. More specifically, the beta-keto ester (IV) may be dissolved in a suitable solvent as listed above. Excess amount of ammonia gas is introduced into the solution at a temperature of 0° to 60° C. Alternatively, a solution containing ammonia dissolved in the above solvent is added to the solution containing the beta-keto ester (IV), and the resultant mixture is reacted at a temperature of 0° to 60° C., to obtain Compound (VII). In this method, it is easier to modify the moiety —X—$R^2$ to obtain the dihydropyridine compounds of formula (I) having a desired —$CH_2$—X—$R^2$ moiety attached to the 6 position of the pyridine ring of the dihydropyridine (I).

The compounds of formula (I), and the intermediates shown in the above Preparation Methods can be isolated and purified by conventional procedures, such as recrystallisation or chromatographic purification.

As the dihydropyridine compounds of this invention possess at least two asymmetric centers, they are capable of occurring in various stereoisomeric forms or configurations. Hence, the compounds can exist in separated (+)- and (−)-optically active forms, as well as in racemic or (+)-mixtures thereof. The present invention includes all such forms within its scope. Individual isomers can be obtained by known methods, such as optically selective reaction or chromatographic separation in the preparation of the final product or its intermediate.

Insofar as the dihydropyridine compounds of this invention are basic compounds, they are capable of forming a wide variety of different salts with various inorganic and organic acids.

The acids which are used to prepare the pharmaceutically acceptable acid addition salts of the aforementioned dihydropyridine base compounds of this invention of formula (I) are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate))salts. The acid addition salts can be prepared by conventional procedures.

The dihydropyridine compounds of the present invention of formula (I) exhibit significant bradykinin receptor-binding activity and therefore, are of value in the treatment of a wide variety of clinical conditions in mammals, especially man. Such conditions include inflammation, cardiovascular disease, pain, common cold, allergies, asthma, pancreatitis, burns, virus infection, head injury, multiple trauma and the like.

Therefore, these compounds are readily adapted to therapeutic use as bradykinin antagonists for the control and/or treatment of any of the aforesaid clinical conditions in mammals, including humans.

The activity of the dihydropyridine compounds of the present invention, as bradykinin antagonists, is determined by their ability to inhibit the binding of bradykinin at its receptor sites in IMR90 cells which express BK2 receptor or A431 cells employing radioactive ligands.

The bradykinin antagonist activity of the dihydropyridine compounds is evaluated by using the standard assay procedure described in, for example, Baenziger N. L., Jong Y -J. I., Yocum S. A., Dalemar L. R., Wilhelm B., Vaurek R., Stewart J. M., Eur. J. Cell Biol., 1992, 58, 71–80. This method essentially involves determining the concentration of the individual compound required to reduce by 50% the amount of radiolabelled bradykinin ligands at their receptor sites in rat, guinea pig or monkey tissues, or A431 or IMR90 cells, thereby affording characteristic $IC_{50}$ values for each compound tested.

More specifically, the assay is carried out as follows. First, rat, guinea pig or monkey ileum tissues are minced and suspended in buffer (25 mM piperazine-N,N'-bis(2-ethanesulfonic acid)(PIPES) adjusted to pH 6.8, containing 0.1 mg/ml of soybean trypsin inhibitor). Then, the tissues are homogenized using a Polytron homogenizer at setting #6 for 30 seconds, and centrifuged at 30,000×g for 20 minutes. The pellets thus obtained are homogenized with the same buffer, and recentrifuged. The tissue pellets, IMR90 cells or A431 cells are suspended in assay buffer (1.25 mM dithiothreitol-1.75 $\mu$g/ml bacitracin-125 $\mu$M o-phenanthroline-6.25 $\mu$M captopril-1.25 mg/ml bovine serum albumin-25 mM PIPES (pH6.8)), to prepare tissue/cell suspensions. Then, 10 $\mu$l of the test compound solution dissolved in DMSO or 12.5 $\mu$M bradykinin are placed in a reaction plate. 15$\mu$ of 8.3 nM [$^3$H]Bradykinin are added to the mixture in the reaction plate. Finally 100 $\mu$l of the tissue or cell suspension are added to the mixture in the reaction plate, and incubated at 25° C. for 1 hour. After incubation, the resultant product in the reaction plates is filtered through 0.1% polyethylenimine presoaked LKB filermat. The filtrate is washed using a Skatron auto cell harvester. The tissue bound radioactivity is determined using a LKB betaplate counter. The $IC_{50}$ value is determined using the equation:

$$\text{Bound}=B_{max}/(1+[I]/IC_{50})$$

wherein [I] means the concentration of the test compound.

All compounds prepared in the Working Examples as described below were tested by this method, and showed an $IC_{50}$ value of 5 nM to 1 $\mu$M with respect to inhibition of binding at its receptor.

The dihydropyridine compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for the treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in $CDCl_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Example 1

Dimethyl 4-(2,6-dichlorophenyl)-6-methyl-2-piperazinylcarbonylmethyl-1,4-dihydro-pyridine-3,5-dicarboxylate A mixture of dimethyl 4-(2,6-dichlorophenyl)-2-methoxycarbonylmethyl-6-methyl-1,4-dihydropyridine-3,5-dicarboxylate(13.9 g, 30 mmol), piperazine(39.2 g, 460 mmol), and dimethylformamide(30 ml) was heated to 100° C. (becomes a solution) and stirred for 1.5 h (longer reaction times result in decomposition). The reaction mixture was cooled briefly, poured into water(800 ml), and extracted with ethyl acetate. The extract was washed thoroughly with water, dried over sodium sulfate, and concentrated to give 12.2 g (84%) of an orange color oil, suitable for use in succeeding steps. It can be purified by column chromatography on silica gel using dichloromethane/methanol: 2/1 as eluent.

$^1$H NMR (CDCl$_3$) δ 2.24 (s, 3H), 2.86 (m, 4H), 3.54 (s, 3H), 3.56 (s, 3H), 3.63 (m, 4H), 4.02 (ABq, J=16 Hz, v=126, 2H), 5.96 (s, 1H), 6.99 (t, J=8 Hz, 1H), 7.26 (m, 2H), 7.94 (s, 1H).

Example 2

Dimethyl 4-(2,6-dichlorophenyl)-6-methyl-2-[4-(tricyclo[4.3.3.0]dodecan-8-one-11-yl)-1-piperazinyl]carbonylmethyl-1,4-dihydropyridine-3,5-dicarboxylate A mixture of dimethyl 4-(2,6-dichlorophenyl)-6-methyl-2-piperazinylcarbonylmethyl-1,4-dihydropyridine-3,5-dicarboxylate (0.50 g, 1.04 mmol), tricyclo[4.3.3.0] dodecan-8,11-dione (0.60 g, 3.12 mmol, prepared according to reported method: Can. J. Chem., 1978, 56, 189), methanol (15 ml), 3A molecular sieves, and NaBH$_3$CN(0.125 g, 2.08 mmol) was refluxed for 50 hr. The reaction mixture was cooled, and quenched with 1N HCl (2 ml). The reaction mixture was partitioned between ethyl acetate/NaHCO$_3$ aqueous solution. The organic layer was separated, washed with NaHCO$_3$ aqueous solution and brine, dried over Na$_2$SO$_4$, and concentrated. The residue was chromatographed on silica gel using 4% methanol in dichloromethane as eluent to afford the desired product as an oil, 390 mg (57%). This material was suitable for further reactions, or could be converted to its hydrochloride salt with HCl gas in ether to afford a white solid, mp 190°–195° C.

$^1$H NMR (CDCl$_3$) δ 1.2–2.0 (m, 12H), 2.19 (s, 3H), 2.24 (m, 4H), 2.37 (m, 4H), 2.82 (m, 1H), 3.47 (s, 3H), 3.49 (s, 3H), 3.59 (m, 4H), 3.90 (ABq, J=15 Hz, v=135, 2H), 5.90 (s, 1H), 6.94 (m, 1H), 7.19 (m, 2H), 7.86 (s, 1H). IR (, KBr): 1720, 1675 cm$^{-1}$. MS m/e: 657 (<1, M$^+$), 512 (19, loss of 2,6-dichlorophenyl), 364 (100), 250 (62), 222 (81), 136 (82), 107 (32), 91 (44). Anal. Calcd for C$_{34}$H$_{41}$N$_3$O$_6$Cl$_2$.2HCl: C, 55.82; H, 5.92; N, 5.74. Found: C, 55.62; H, 5.62; N, 6.03.

Example 3

Dimethyl 4-(2,6-dichlorophenyl)-6-methyl-2-[4-(tricyclo[4.3.3.0]dodecan-8-ol-11-yl)-1-piperazinyl]carbonylmethyl-1,4-dihydropyridine-3,5-dicarboxylate A mixture of dimethyl 4-(2,6-dichlorophenyl)-6-methyl-2-piperazinylcarbonylmethyl-1,4-dihydropyridine-3,5-dicarboxylate(0.20 g, 0.415 mmol), tricyclo[4.3.3.0]dodecan-8,11-dione (0.24 g, 1.245 mmol, prepared according to reported method: Can. J. Chem., 1978, 56, 189), methanol (10 ml), 3A molecular sieves, and NaBH$_3$CN (0.052 g, 0.83 mmol) was refluxed for 4 days. After cooling down, NaBH$_4$(16 mg, 0.415 mmol) was added to the reaction mixture and stirred at room temperature for 2 days. The reaction mixture was quenched with 1N HCl (2 ml). The reaction mixture was partitioned between ethyl acetat6-205e/NaHCO$_3$ aqueous solution. The organic layer was separated, washed with NaHCO$_3$ aqueous solution and brine, dried over Na$_2$S$_O_4$, and concentrated. The residue was chromatographed on silica gel using 15% methanol in dichloromethane as eluent to afford the desired product as an oil, which was converted to its hydrochloride salt with HCl gas in ether to afford 52 mg(18%) of solid, mp 185°–195° C.

$^1$H NMR (CDCl$_3$) δ 1.2–2.0 (m, 16H), 2.19 (s, 3H), 2.4 (m, 5H), 3.47 (s, 3H), 3.49 (s, 3H), 3.62 (m, 4H), 3.89 (ABq, J=15 Hz, v=108, 2H), 4.4 (m, 1H), 5.90 (s, 1H), 6.95 (m, 1H), 7.20 (m, 2H), 7.86 (s, 1H). IR (KBr): 1697 cm$^{-1}$. MS m/e: 659 (<1, M$^+$–1), 514 (24, loss of 2,6-dichlorophenyl), 119 (67), 93 (85), 91 (75), 55 (66). High Res. FAB MS: Calcd for C$_{34}$H$_{43}$N$_3$O$_6$Cl$_2$: 660.2607. Found: 660.26569.

Example 4

Dimethyl 4-(2,6-dichlorophenyl)6-methyl-2-[4-(tricyclo[4.3.3.0]dodecan-8-amine-11-yl)-1-piperazinyl]carbonylmethyl-1,4-dihydropyridine-3,5-dicarboxylate A mixture of dimethyl 4-(2,6-dichlorophenyl)-6-methyl-2-[4-(tricyclo[4.3.3.0]dodecan-8-one-11-yl)-1-piperazinyl]carbonylmethyl-1,4-dihydropyridine-3,5-dicarboxylate (0.39 g, 0.592 mmol), ammonium acetate(0.456 9, 5.92 mmol), methanol(6 ml), and NaBH$_3$CN (0.074 g, 1.18 mmol) was stirred for 2.5 days. The reaction mixture was quenched with 1N HCl (2 ml). The reaction mixture was partitioned between ethyl acetate/NaHCO$_3$ aqueous solution. The organic layer was separated, washed with NaHCO$_3$ aqueous solution and brine, dried over Na$_2$SO$_4$, and concentrated to give a gummy solid. In order to effect purification, this material was first converted to its N-t-Boc derivative as follows: The above gum was dissolved in 1,2-dichloroethane (10 ml) and treated with di-t-butyl dicarbonate (116 mg, 0.530 mmol) at room temperature for 14 h. The reaction mixture was concentrated and the residue was chromatographed on silica gel using 15% methanol in dichloromethane as eluent (product is Rf=0.7 in this system) to afford an oil, 350 mg (78% overall).

¹H NMR (CDCl₃) δ 1.2–2.0 (m, 16H), 1.39 (s, 9H), 2.20 (s, 3H), 2.36 (m, 4H), 2.36 (m, 4H), 2.6 (m, 1H), 3.48 (s, 3H), 3.50 (s, 3H), 3.62 (m, 4H), 3.96 (ABq, J=15 Hz, v=128, 2H), 4.5 (m, 1H), 6.94 (m, 1H), 7.22 (m, 2H), 7.90 (s, 1H). FAB MS m/e: 759 (35, M⁺), 612 (8, loss of 2,6-dichlorophenyl), 364 (30), 307 (37), 250 (100).

To a stirred solution of this oil in dichloromethane (5 ml) was added trifluoroacetic acid (5 ml) at 0° C. After 1 h stirring, the reaction mixture was poured carefully into NaHCO₃ aqueous solution and extracted with dichloromethane. The extract was dried over Na₂SO₄ and concentrated to give a gum. This gum was converted to its hydrochloride salt using HCl gas saturated ether to afford 164 mg (55%) of solid, mp 210°–220° C.

¹H NMR (CDCl₃) δ 1.2–2.0 (m, 16H), 2.20 (s, 3H), 2.35 (m, 4H), 2.55 (m, 1H), 2.76 (m, 1H), 3.49 (s, 3H), 3.50 (s, 3H), 3.61 (m, 4H), 3.95 (m, 2H, these protons, adjacent to the piperazine amide nitrogen, are split in a complex pattern by virtue of the isomers on the tricyclic ring), 5.91 (s, 1H), 6.94 (m, 1H), 7.22 (m, 2H), 7.9–8.0 (m, 1H, this of the dihydropyridine ring is a complex pattern as above). IR (KBr): 1698 cm⁻¹. FAB MS m/e: 659 (M⁺). High Res. FAB MS: Calcd for C₃₄H₄₄N₄O₅Cl₂: 659.27668. Found: 659.2748. Anal. Calcd for C₃₄H₄₄N₄O₅Cl₂.2.5HCl.0.5H₂O: C, 53.75; H, 6.30; N, 7.37. Found: C, 53.94; H, 5.94; N, 6.79.

Example 5
Dimethyl 4-(2,6-dichlorophenyl)-2-{4-[8-(2-methoxybenzamido)-tricyclo[4.3.3.0]-dodecan-11-yl]-1-piperazinyl}carbonylmethyl-6-methyl-1,4-dihydropyridine-3,5-dicarboxylate To a stirred solution of dimethyl 4-(2,6-dichlorophenyl)-6-methyl-2-[4-(tricyclo[4.3.3.0]-dodecan-8-amine-11-yl)-1-piperazinyl]carbonylmethyl-1,4-dihydropyridine-3,5-dicarbo-xylate(100 mg, 0.137 mmol) and triethylamine(38 μl, 0.273 mmol) in dichloroethane(5 ml) was added 2-methoxybenzoyl chloride(24 μl, 0.164 mmol) and the reaction mixture was stirred at room temperature for 2.5 days. The reaction mixture was washed with NaHCO₃ aqueous solution and brine, dried, and concentrated. The residue was purified by column chromatography on silica gel using 10% methanol in dichloromethane as eluent to afford an oil, which was converted to the hydrochloride salt with HCl gas saturated ether to give 40 mg(35%) of solid, mp 175°–185° C.

¹H NMR (CDCl₃) δ 1.2–2.0 (m, 16H), 2.21 (s, 3H), 2.50 (m, 4H), 2.8 (m, 1H), 3.49 (s, 3H), 3.51 (s, 3H), 3.7 (m, 4H), 4.02 (s, 3H), 4.2 (m, 2H), 4.4 (m, 1H), 5.95 (s, 1H), 6.9–8.1 (m, 7H), 7.87 (br s, 1H). IR (KBr): 1680 cm⁻¹. FAB MS m/e: 793 (M⁺). High Res. FAB MS: Calcd for C₄₂H₅₀N₄O₇Cl₂: 793.31345. Found: 793.3190. Anal. Calcd for C₄₂H₅₀N₄O₇Cl₂.HCl.0.5H₂O: C, 58.85; H, 6.35; N, 6.54. Found: C, 58.80; H, 6.06; N, 6.15.

Example 6
Dimethyl 2-[4-(3-benzyl-3-azabicyclo[3.3.1]nonan-9-yl)-1-piperazinyl]carbonylmethyl-4-(2,6-dichlorophenyl)-6-methyl-1,4-dihydropyridine-3,5-dicarboxylate
A. 3-Benzyl-3-azabicyclo[3.3.1]nonan-9-one A mixture of benzylamine(17.25 ml, 0.683 mol), acetic acid(182 ml), c-HCl (13.25 ml), cyclohexanone (13.25 ml, 0.127 mol), and aqueous formaldehyde solution (4.1M, 31.25 ml, 1.25 mol) was stirred at 80° C. for 2 h, cooled, and concentrated. The residue was partitioned between ether and water, and the pH was adjusted to 8 with solid Na₂CO₃. The reaction mixture was extracted with dichloromethane and the extract was dried over Na₂SO₄ and concentrated. This residue was taken up in 37 ml ethanol and treated with acetic anhydride (12.5 ml, 0.530 mol), stirred at room temperature for 2 h, treated with c-HCl (15 ml), and stirred at room temperature for 2 h. The reaction mixture was concentrated, and the residue taken up in water and washed with dichloromethane. The aqueous layer was adjusted to pH 8 with solid Na₂CO₃ and extracted with dichloromethane and ethyl acetate. The extracts combined was dried over Na₂SO₄ and concentrated. The residue was chromatographed on silica gel using hexane/ethyl acetate: 10/1 as eluent to afford an oil which solidified on standing, mp 48°–50.5° C., 2.4 g (20.5%).

¹H NMR (CDCl₃) δ 1.23 (m, 1H), 1.99 (m, 2H), 2.12 (m, 2H), 2.33 (br s, 2H), 2.55 (m, 2H), 2.94 (m, 1H), 3.13 (m, 2H), 3.44 (s, 2H), 7.2–7.4 (m, 4H).
B. 3-Benzyl-9-piperazinyl-3-azabicyclo[3.3.1]nonane A mixture of 3-benzyl-3-azabicyclo[3.3.1]nonan-9-one (0.72 g, 3.14 mmol), methanol (25 ml), piperazine(2.71 g, 31.4 mmol), several 3A molecular sieves, and NaBH₃CN (0.39 g, 6.28 mmol) was refluxed for 60 hr, cooled, and concentrated. The residue was taken up in 1N HCl (50 ml), washed with ethyl acetate, the pH adjusted to 12 with 1N NaOH aqueous solution, and extracted with dichloromethane. The extract was dried over Na₂SO₄ and concentrated to afford 0.72 g (72% crude) of an oil, which was used directly in the following step.

¹H NMR (CDCl₃) δ 1.3–2.0 (m, 1OH), 2.1–2.7 (m, 6H), 2.84 (m, 4H), 2.94 (m, 1H), 3.35 (s, 2H), 7.2–7.4 (m, 5H). MS m/e: 298 (9, M⁺+1), 269 (36), 134 (40), 91 (100), 56 (48).
C. Dimethyl 2-[4-(3-benzyl-3-azabicyclo[3.3.1]nonan-9-yl)-1-piperazinyl]carbonylmethyl4-(2,6-dichlorophenyl)-6-methyl-1,4-dihydropyridine-3,5-dicarboxylate A mixture of dimethyl 4-(2,6-dichlorophenyl)-2-methoxycarbonylmethyl-6-methyl-1,4-dihydropyridine-3,5-dicarboxylate (1.04 g, 2.42 mmol) and a solution of KOH (0.67 g) in aqueous ethanol (20 ml, ethanol/water: 9/1) was stirred at room temperature for 30 min. After evaporation of the solvent, the residue was taken up in water, and the pH adjusted to 1 with 1N HCl. The mixture was extracted with ethyl acetate, and the extract was washed with water and brine, dried over Na₂SO₄, and concentrated. The resulting acid was dissolved in dichloromethane (30 ml). To this solution was added 3-benzyl-9-piperazinyl-3-azabicyclo-[3.3.1]nonane(0.72 9, 2.42 mmol) and 1-ethyl-3-(3-dimethylaminopropyl) carbodiimide hydrochloride (0.70 g, 3.64 mmol) and stirred at room temperature for 14 hr. The reaction mixture was washed with water and NaHCO₃ aqueous solution, dried over Na₂SO₄, and concentrated. The residue was chromatographed on silica gel using 5% methanol in dichloromethane as eluent (Rf=0.6 for product in this system) to afford 0.85 g (50%) of an oil, which was converted to the hydrochloride salt, mp192°–202° C.

¹H NMR (CDCl₃) δ 1.3–1.5 (m, 3H), 1.86 (m, 5H), 2.1–2.2 (m, 2H), 2.22 (s, 3H), 2.35 (m, 4H), 2.61 (m, 1H), 2.94 (m, 2H), 3.35 (s, 2H), 3.49 (s, 3H), 3.51 (s, 3H), 3.63 (m, 4H), 3.97 (ABq, J=15 Hz, v=105, 2H), 5.91 (s, 1H), 6.94 (m, 1H), 7.20 (m, 2H), 7.28 (m, 5H), 7.94 (s, 1H). ¹³C NMR (CDCl₃) δ 19.6, 21.4, 24.7, 30.6, 32.2, 38.0, 42.4, 46.4, 48.9, 49.5, 50.4, 50.7, 59.8, 63.4, 65.1, 99.9, 127.3, 128.2, 128.6, 137.1, 139.5, 139.8, 143.0, 145.8, 167.8, 168.0, 168.2. IR (KBr): 1697 cm⁻¹. MS m/e: 694 (2, M⁺), 549 (20), 231 (31), 230 (30), 140 (31), 91 (100). Anal. Calcd for C₃₇H₄₄N₄O₅Cl₂.2HCl.1.25H₂O: C, 56.28; H, 6.18; N, 7.08. Found: C, 56.43; H, 6.48; N, 6.68.

Example 7
Dimethyl-{4-[3-(1-chloroethoxycarbonyl)-3-azabicyclo[3.3.1]nonan-9-yl]-1-pipera-zinyl}carbonylmethyl-4-(2,6-dichlorophenyl)-6-methyl-1,4-dihydropyridine-3,5-dicarboxylate A mixture of dimethyl 2-[4-(3-benzyl-3-azabicyclo[3.3.1]nonan-9-yl)-1-piperazinyl]-carbonylmethyl-4-(2,6-dichlorophenyl)-6-methyl-1,4-dihydropyridine-3,5-dicarboxylate (0.85 g, 1.22 mmol) and 1-chloroethyl chloroformate (0.19 ml, 1.71 mmol) in dichloroethane (20 ml) was refluxed for 1.6 h. The reaction mixture was cooled, concentrated, and chromatographed on silica gel using 4% methanol in dichloromethane as eluent (Rf=0.4 for product in this system, vs. 0.6 for starting material) to afford 0.53 g (61%) of an oil.

$^1$H NMR (CDCl$_3$) δ 1.3–1.5 (m, 3H), 1.78 (d, J=6 Hz, 3H), 1.86 (m, 5H), 2.21 (s, 3H), 2.37 (m, 4H), 3.02 (m, 2H), 3.49 (s, 3H), 3.51 (s, 3H), 3.67 (m, 4H), 3.97 (m, 2H), 4.18 (m, 2H), 5.92 (s, 1H), 6.58 (q, J=6 Hz, 1H), 6.96 (m, 1H), 7.2 (m, 2H), 7.88 (s, 1H). IR (KBr): 1699 cm$^{-1}$. FAB MS m/e: 605 (M$^+$—COCH(CH$_3$)Cl) Anal. Calcd for C$_{33}$H$_{41}$N$_4$O$_7$Cl$_3$HCl.H$_2$O: C, 51.71; H, 5.79; N, 7.31. Found: C, 51.97; H, 6.03; N, 6.97.

Example 8

Dimethyl 2-[4-(3-azabicyclo[3.3.1]nonan-9-yl)-1-piperazinyl]carbonylmethyl-4-(2,6-dichlorophenyl)-6-methyl-1,4-dihydropyridine-3,5-dicarboxylate A mixture of dimethyl 2-{-[3-(1-chloroethoxycarbonyl)-3-azabicyclo[3.3.1]nonan-9-yl]-1-piperazinyl}carbonylmethyl4-(2,6-dichlorophenyl)-6-methyl-1,4-dihydropyridine-3,5-dicarboxylate (0.53 g, 0.708 mmol) and methanol (30 ml) was refluxed for 1 h. The reaction mixture was cooled and concentrated. The residue was taken up in dichloromethane and precipitated with ether to afford the product as a solid, mp 225°–230° C., 0.30 g (62.5%).

$^1$H NMR (CDCl$_3$) δ 1.3–1.5 (m, 3H), 1.86 (m, 7H), 2.21 (s, 3H), 2.37 (m, 4H), 2.82 (m, 1H), 2.95 (m, 2H), 3.49 (s, 3H), 3.50 (s, 3H), 3.67 (m, 4H), 3.99 (ABq, J=14 Hz, v=120, 2H), 5.92 (s, 1H), 6.96 (m, 1H), 7.2 (m, 2H), 7.95 (s, 1H). IR (KBr): 1699 cm$^{-1}$. FAB MS m/e: 605 (M$^+$+1). High Res. FAB MS: Calcd for C$_{30}$H$_{38}$N$_4$O$_5$Cl$_2$: 604.2219. Found: 604.1186. Anal. Calcd for C$_{30}$H$_{38}$N$_4$O$_5$Cl$_2$.3HCl.1.5H$_2$O: C, 48.47; H, 5.97: N, 7.55. Found: C, 48.81; H, 5.85; N, 7.02.

Example 9

Dimethyl 2-[4-(3-acetyl-3-azabicyclo[3.3.1]nonan-9-yl)-1-piperazinyl]carbonylmethyl-4-(2,6-dichlorophenyl)-6-methyl-1,4-dihydropyridine-3,5-dicarboxylate A mixture of dimethyl 2-[4-(3-azabicyclo[3.3.1]nonan-9-yl)-1-piperazinyl]carbonylmethyl-4-(2,6-dichlorophenyl)-6-methyl-1,4-dihydropyridine-3,5-dicarboxylate (0.10 g, 0.147 mmol), 4-dimethylaminopyridine (72 mg, 0.589 mmol), and acetyl chloride (0.016 ml, 0.021 mmol) in dichloroethane (5 ml) was stirred at room temperature for 1 h. The reaction mixture was washed with NaHCO$_3$ aqueous solution, dried over Na$_2$SO$_4$, and concentrated. The residue was chromatographed on silica gel using 10% methanol in dichloromethane as eluent to afford an oil, which solidified on standing and was collected after trituration with isopropyl ether to give 54 mg (57%) of solid, mp 269°–270° C. (dec).

$^1$H NMR (CDCl$_3$) δ 1.3–1.5 (m, 3H), 1.86 (m, 5H), 2.06 (s, 3H), 2.20 (s, 3H), (s, 3H), 2.37 (m, 4H), 2.74 (m, 1H), 3.25 (m, 2H), 3.48 (s, 3H), 3.50 (s, 3H), 3.67 (m, 4H), 3.99 ((m, 2H), 4.61 (m, 2H), 5.92 (s, 1H), 6.96 (m, 1H), 7.2 (m, 2H), 7.87 (s, 1H). IR (KBr): 1698 cm$^{-1}$. MS m/e: 501 (10, M$^+$-2,6-dichlorophenyl), 354 (39), 252 (56), 251 (92), 166 (31), 124 (100), 95 (69), 67 (33), 56 (36), 55 (38). Anal. Calcd for C$_{30}$H$_{38}$N$_4$O$_5$Cl$_2$.0.75H$_2$O: C, 58.14; H, 6.32; N 8.47. Found: C, 58.37; H, 6.14; N, 8.08.

Example 10

Dimethyl 2-[4-(8-benzyl-8-azabicyclo[3.2.1]octan-3-yl)-1-piperazinyl]carbonylmethyl-4-(2,6-dichlorophenyl)-6-methyl-1,4-dihydropyridine-3.5-dicarboxylate A. 8-Benzyl-8-azabicyclo[3.2.1]octan-3-one This was prepared according to the reported method (*Chem. Abs.*, 1958, 53, 432e). A mixture of 2,5-dimethoxytetrahydrofuran (13 ml, 0.1 mol), 2 drops of c-HCl and water (10 ml) was stirred at room temperature for 1 h, then treated with water(10 ml), acetone-1,3-dicarboxylic acid (14.6 g, 0.1 mol), and benzylamine (10.9 ml, 0.1 mol). After the initial foaming had subsided, the pH was adjusted to 5 with 1N HCl, and stirring was continued for 14 h. The reaction mixture was adjusted to pH 1, washed with ethyl acetate, filtered through celite, and then adjusted to pH 12 with NaOH, and extracted with ethyl acetate. The extract was dried over Na$_2$SO$_4$ and concentrated to afford 14.5 g (67% crude) of an oil, which was used for next reaction without further purification.

$^1$H NMR (CDCl$_3$) δ 1.60 (m, 2H), 2.0–2.2 (m, 4H), 2.65 (m, 2H), 3.46 (br. s, 2H), 3.71 (s, 2H), 7.2–7.4 (m, 5H).

B. 8-Benzyl-3-piperazinyl-8-azabicyclo[3.2.1]octane

This was prepared in 36% yield as an oil according to a procedure similar to that described in Example 6.

$^1$H NMR (CDCl$_3$) δ 1.4–1.7 (m, 6H), 1.9–2.1 (m, 4H), 2.44 (m, 4H), 2.83 (m, 4H), 3.19 (m, 1H), 3.54 (s, 2H), 7.2–7.4 (m, 5H). MS m/e: 285 (5, M$^+$), 172 (28), 160 (23), 159 (26), 158 (28), 113 (43), 91 (100).

C. Dimethyl 2-[4-(8-benzyl-8-azabicyclo[3.2.1]octan-3-yl)-1-piperazinyl]carbonylmethyl-4-(2,6-dichlorophenyl)-6-methyl-1,4-dihydropyridine-3,5-dicarboxylate This was prepared in 10% yield as the hydrochloride salt, mp 200°–210° C. according to a procedure similar to that described in Example 6.

$^1$H NMR (CDCl$_3$) δ 1.4–1.7 (m, 6H), 1.9–2.1 (m, 4H), 2.21 (s, 3H), 2.47 (m, 5H), 3.21 (m, 2H), 3.40 (s, 2H), 3.49 (s, 3H), 3.51 (s, 3H), 3.61 (m, 4H), 3.97 (ABq, J=15 Hz, v=156, 2H), 5.92 (s, 1H), 6.94 (m, 1H), 7.2–7.4 (m, 7H), 7.93 (s, 1H). IR (KBr): 1700 cm$^{-1}$. MS m/e: 680 (<1, M$^+$), 535 (1, loss of 2,6-dichlorophenyl), 215 (44), 160 (31), 91 (100). 84 (34), 58 (43). Anal. Calcd for C$_{35}$H$_{42}$N$_4$O$_5$Cl$_2$.2HCl.2H$_2$O: C, 54.69; H, 6.12; N, 7.09. Found: C, 54.76; H, 6.28; N, 7.13.

Example 11

Dimethyl 2-[4-(3-benzyl-3-azatricyclo[3.3.3.0]undecan-2,4-dione-7-yl)-1-piperazinyl]carbonylmethyl-4-(2,6-dichlorophenyl)-6-methyl-4-dihydropyridine-3,5-dicarboxylate A. 3-Benzyl-3-azabicyclo[3.3.0]oct-1-ene-2,4-dione This was prepared according to the reported method (*Syn. Commun.*, 1990, 20, 1607). A mixture of cyclopentene-1,2-dicarboxylic acid anhydride (1.0 g, 7.24 mmol) and benzylamine (0.79 ml, 7.24 mmol) in dry toluene (20 ml) was heated at 45°–50° C. for 1 h. After cooled down, the precipitate appeared was collected by filtration, washed with toluene and dried to afford a solid, mp 164°–167° C., 1.75 g (99%). The solid was taken up in 20 ml acetone, treated with triethylamine(2.02 ml, 14.48 mmol), heated to reflux, then treated with acetic anhydride (1.02 ml, 10.86 mmol). The reaction mixture was refluxed for 3 days. The reaction mixture was cooled and concentrated. The residue was partitioned between ethyl acetate and NaHCO$_3$ aqueous solution, and the organic layer was washed with NaHCO$_3$ aqueous solution and brine, dried over Na$_2$SO$_4$, and concentrated. The product showed Rf=0.3 in 20% ethyl acetate in hexane. The residue was chromatographed on silica gel with this system to afford 1.18 g (72%) of the product as an oil.

$^1$H NMR (CDCl$_3$) δ 2.41 (m, 2H), 2.63 (m, 4H), 4.60 (s, 2H), 7.2–7.4 (m, 5H).

B. 3-Benzyl-7-methylene-3-azatricyclo[3.3.3.0]undecane-2,4-dione

This was prepared according to the reported method (*J. Am. Chem. Soc.*, 1983, 105, 2315; *Tet. Lett.*, 1986, 1445). A mixture of 3-benzyl-3-azabicyclo[3.3.0]oct-1-ene-2,4-dione (1.18 g, 5.20 mmol), 3-acetoxy-2-trimethylsilylmethylpropene (1.08 ml, 5.20 mmol), palladium diacetate (58 mg, 0.26 mmol), and triisopropyl phosphite (0.43 ml, 1.73 mmol) in dry toluene (10 ml) was refluxed with stirring for 5 days. The reaction mixture was cooled and concentrated. The residue was chromatographed on silica gel with hexane/ethyl acetate to afford 1 g (68%) of an oil.

$^1$H NMR (CDCl$_3$) δ 1.42 (m, 1H), 1.68 (m, 2H), 1.75 (m, 1H), 2.15 (m, 2H), 2.53 (ABq, J=15 Hz, v=90, 2H), 4.57 (s, 2H), 4.79 (m, 2H), 7.23 (m, 5H). IR (CHCl$_3$): 1710 cm$^{-1}$. MS m/e: 281 (72, M$^+$), 119 (68), 105 (39), 93 (32), 91 (100), 79 (40), 77 (41), 65 (40).

C. 3-Benzyl-3-azatricyclo[3.3.3.0]undecane-2,4,7-trione

To a stirred solution of 3-Benzyl-7-methylene-3-azatricyclo[3.3.3.0]undecane-2,4-dione(1 g, 3.56 mmol) in dichloromethane (40 ml) was bubbled ozone gas at 0° C. for 20 minutes (until a light blue color persisted). Then the reaction mixture was purged with oxygen and nitrogen. The reaction mixture was treated with acetic acid (5 ml), zinc metal (100 mg 100 mesh), and water (1 ml). The reaction mixture was stirred at room temperature for 30 min (negative KI/starch test) and poured into ethyl acetate and water. The organic layer was washed with water, NaHCO$_3$ aqueous solution, and brine, dried over Na$_2$SO$_4$, and concentrated to afford 1.46 g (100% crude overall yield for 2 steps) of an oil, which contained a small amount of the corresponding alcohol. Tlc for product, Rf=0.8 in ethyl acetate.

$^1$H NMR (CDCl$_3$) δ 1.6–2.0 (m, 6H), 2.4–2.7 (m, 4H), 4.62 (s, 2H), 7.2–7.4 (m, 5H). IR (CHCl$_3$): 1740, 1700 cm$^{-1}$. MS m/e: 284 (31), 283 (67, M$^+$), 282 (56), 198 (30), 192 (31), 132 (47), 122 (36), 121 (35), 107 (40), 106 (52), 95 (44), 94 (61), 93 (63), 91 (100), 79 (63), 77 (62), 65 (63), 51 (41).

D. Dimethyl 2-[4-(3-benzyl-3-azatricyclo[3.3.3.0] undecane-2,4-dione-7-yl)-1-piperazinyl]carbonylmethyl-4-(2,6-dichlorophenyl)-6-methyl-1,4-dihydropyridine-3,5-dicarboxylate This was prepared in 14% yield as the hydrochloride salt, mp 145°–153° C. according to a procedure similar to that described in Example 6.

$^1$H NMR (CDCl$_3$) δ 1.4–1.7 (m, 10H), 2.17 (s, 3H), 2.48 (m, 5H), 3.46 (s, 3H), 3.47 (s, 3H), 3.6 (m, 4H), 3.96 (ABq, J=14 Hz, v=123, 2H), 4.52 (s, 2H), 5.89 (s, 1H), 6.92 (m, 1H), 7.2–7.4 (m, 7H), 7.69 (s, 1H). IR (CHCl$_3$): 1693 cm$^{-1}$. FAB MS m/e: 749 (66, M$^+$), 603 (68, loss of 2,6-dichlorophenyl), 250 (100). Anal. Calcd for C$_{39}$H$_{42}$N$_4$O$_7$Cl$_2$.HCl.0.5H$_2$O: C, 58.91; H, 5.58; N, 7.05. Found: C, 58.66; H, 5.71; N, 6.73.

Example 12

Dimethyl 2-[4-(3-benzyl-3-azatricyclo [3.3.3.0]undecan-7-yl)-1-piperazinyl]carbonylmethyl-4-(2,6-dichlorophenyl)-6-methyl-1,4-dihydronpyridine-3,5-dicarboxylate A. 3-Benzyl-7-piperazinyl-3-azatricyclo[3.3.3.0]undecane-2,4-dione A mixture of 3-benzyl-3-azatricyclo[3.3.3.0]undecane-2,4,7-trione (0.50 g, 1.77 mmol), piperazine (1.52 g, 17.7 mmol), methanol (30 ml), several 3A molecular sieves, and NaBH$_3$CN (0.22 g, 3.54 mmol) was refluxed for 16 h. The reaction mixture was cooled and concentrated. The residue was taken up in ethyl acetate, washed with water, NaHCO$_3$ aqueous solution, and brine, dried over Na$_2$SO$_4$, and concentrated to give 360 mg (58% crude) of an oil.

H NMR (CDCl$_3$) δ 1.7–2.2 (10H), 2.36 (m, 4H), 2.7–2.9 (m, 4H), 4.57 (ABq, 2H), 7.2–7.4 (m, 5H).

B. 3-Benzyl-7-piperazinyl-3-azatricyclo[3.3.3.0] undecane

To a stirred solution of 3-benzyl-3-azatricyclo[3.3.3.0] undecane-2,4,7-trione (360 mg, 1.02 mmol) in dry tetrahydrofuran (8 ml) was added a solution of lithium aluminum hydride (1M solution in tetrahydrofuran, 4.08 ml, 4.08 mmol) dropwise at 0° C. The reaction mixture was stirred at room temperature for 36 hr. The reaction mixture was quenched carefully with 10% aqueous ammonium hydroxide, diluted with ethyl acetate, and filtered through celite. The filtrate was washed with water and brine, dried over Na$_2$SO$_4$, and concentrated to give 250 mg (75%) of the oil, which was used directly for the next reaction.

$^1$H NMR (CDCl$_3$) δ 1.4–22.0 (m, 10H), 2.49 (m, 8H), 2.8–3.0 (m, 5H), 3.49 (m, 7.4 (m, 5H). MS m/e: 325 (15, M$^+$), 295 (100), 269 (45), 235 (41), 234 (60), 198 (50), 120(42). High Res. MS: Calcd for C$_{21}$H$_{31}$N$_3$: 325.2516. Found: 325.2519.

C. Dimethyl 2-[4-(3-benzyl-3-azatricyclo[3.3.3.0] undecan-7-yl)-1-piperazinyl]carbo-nylmethyl-4-(2,6-dichlorophenyl)6-methyl-1,4-dihydropyridine-3,5-dicarboxylate This was prepared according to a procedure similar to that described in Example 6. to afford two isomers, presumed to have the piperazine ring cis or trans to the benzylamine moiety. They were converted to their hydrochloride salts. Isomer A: mp 215°–220° C., 4% yield:

$^1$H NMR (CDCl$_3$) δ 1.2–2.0 (m, 10H), 2.22 (s, 3H), 2.44 (m, 4H), 2.59 (m, 1H), 2.8 (m, 2H), 3.50 (s, 3H), 3.52 (s, 3H), 3.6 (m, 4H), 3.98 (ABq, J=15 Hz, v=142, 2H), 5.39 (s, 1H), 6.97 (m, 1H), 7.2–7.4 (m, 7H), 7.91 (s, 1H). IR (KBr): 1700 cm$^{-1}$. FAB MS m/e: 721 (100, M$^+$), 575 (20). FAB High Res. MS: Calcd for C$_{39}$H$_{47}$N$_4$O$_5$Cl$_2$: 721.2923. Found: 721.2916. Isomer B: mp 179°–185° C., 3% yield:

$^1$H NMR (CDCl$_3$) δ 1.2–2.0 (m, 8H), 2.18 (m, 2H), 2.22 (s, 3H), 2.49 (m, 5H), 2.8 (m, 2H), 3.50 (s, 3H), 3.52 (s, 3H), 3.6 (m, 4H), 3.99 (ABq, J=15 Hz, v=140, 2H), 5.94 (s, 1H), 6.99 (m, 1H), 7.2–7.4 (m, 7H), 7.95 (s, 1H). IR (KBr): 1699 cm$^{-1}$. FAB MS m/e: 721 (60, M$^+$), 575 (10), 258 (100). FAB High Res. MS: Calcd for C$_{39}$H$_{47}$N$_4$O$_5$Cl$_2$: 721.2923. Found: 721.2920.

Example 13

Dimethyl 2-{4-[3-(1-chloroethoxylcarbonyl)-3-azatricyclo [3.3.3.0]undecan-7-yl]-1-piperazinyl}carbonylmethyl-4-(2, 6-dichlorophenyl)-6-methyl-1,4-dihydropyridine-3,5-dicarboxylate A mixture of dimethyl 2-[4-(3-benzyl-3-azatricyclo [3.3.3.0]undecan-7-yl)-1-pipera-zinyl]carbonylmethyl-4-(2, 6-dichlorophenyl)-6-methyl-1,4-dihydropyridine-3,5-dicarboxylate (383 mg, 0.531 mmol) and 1-chloroethyl chloroformate (0.81 ml, 0.744 mmol) in 1,2-dichloroethane (10 ml) was refluxed for 1.6 h. The reaction mixture was cooled, concentrated, and chromatographed on silica gel using 7% methanol in dichloro-methane as eluent to afforded 200 mg (51%) of an oil, which was converted to the hydrochloride salt, mp 230°–235° C.

$^1$H NMR (CDCl$_3$) δ 1.2–2.0 (m, 10H), 2.17 (s, 3H), 2.40 (m, 5H), 2.94 (m, 2H), 3.45 (s, 3H), 3.47 (s, 3H), 3.6 (m, 6H), 4.18 (m, 2H), 5.89 (s, 1H), 6.92 (m, 1H), 1H), 7.2 (m, 2H), 7.81 (s, 1H). IR (KBr): 1699 cm$^{-1}$. FAB MS m/e: 631 (M$^+$—COCH(CH$_3$)Cl). Anal. Calcd for C$_{35}$H$_{43}$N$_4$O$_7$Cl$_3$.HCl.3.5H$_2$O: C, 50.19; H, 6.14; N, 6.69. Found: C, 50.26; H, 6.07; N, 6.89.

Example 14

Dimethyl 2-[4-(3-azatricyclo[3.3.3.0]undecan-7-yl)-1-piperazinyl]carbonylmethyl)-4-(2,6-dichlorophenyl)-6-methyl-1,4-dihydropyridine-3,5-dicarboxylate A mixture of dimethyl 2-{4-[3-(1-chloroethylcarbonyl)-3-azatricyclo-[3.3.3.0]undecan-7-yl]-1-piperazinyl}carbonylmethyl-4-(2,6-dichlorophenyl)-6-methyl-1,4-dihydropyridine-3,5-dicarboxylate (111 mg, 0.15 mmol) and methanol (15 ml) was refluxed for 1 h. The reaction mixture was cooled and concentrated. The residue was taken up in ethyl acetate/dichloromethane, washed with $NaHCO_3$ aqueous solution and brine, dried over $Na_2SO_4$, and concentrated to give an oil, which was converted to the hydrochloride salt using HCl gas in ether to afford 87 mg (82%) of a solid, mp 220°–230° C.

$^1$H-NMR (CDCl$_3$) δ 1.2–2.0 (m, 10H), 2.19 (s, 3H), 2.40 (m, 7H), 2.93 (m, 2H), 3.47 (s, 3H), 3.49 (s, 3H), 3.6 (m, 6H), 3.94 (ABq, J=14 Hz, v=150, 2H), 5.91 (s, 1H), 6.92 (m, 1H), 7.2 (m, 2H), 7.87 (s, 1H). IR (KBr): 1699 cm$^{-1}$. FAB MS m/e: 631 (M$^+$). High Res. FAB MS: Calcd for $C_{32}H_{40}N_4O_5Cl_2$: 631.2454. Found: 631.2444. Anal. Calcd for $C_{32}H_{40}N_4O_5Cl_2.2HCl.2.5H_2O$: C, 51.28; H, 6.32; N, 7.47. Found: C, 51.06; H, 5.93; N, 6.90.

Example 15

Dimethyl 4-(2,6-dichlorophenyl)-2-(4-methyl-1-piperazinyl)carbonylmethyl-6-(2-phenylethyl)-1,4-dihydropyridine-3,5-dicarboxylate A mixture of dimethyl 4-(2,6-dichlorophenyl)-2-methoxycarbonylmethyl-6-(2-phenylethyl)-1,4-dihydropyridine-3,5-dicarboxylate (3.9 g, 7.52 mmol), methanol(35 ml), water (5 ml), and 6N NaOH (2.51 ml, 15.05 mmol) was stirred at room temperature for 1.25 h. The reaction mixture was diluted with dichloromethane (100 ml) followed by addition of 6 NHCl (3 ml) and water (100 ml). The organic layer separated was washed twice with water and brine, dried over $Na_2SO_4$, and concentrated to 50 ml. To this solution was added N-methylpiperazine (1.25 ml, 11.28 mmol) and 1-ethyl-3-(3-dimethylaminopropyl)carbodiimide hydrochloride (2.162 g, 11.28 mmol) at 0° C. and stirred for 0.5 h, then ice bath was removed and stirring was continued at room temperature overnight. The reaction mixture was washed with water, $NaHCO_3$ aqueous solution and brine, and dried over $Na_2SO_4$. The solvent was evaporated and the crude product was chromatographed on 234 g silica gel (dichloromethane/ethyl acetate: 22/3 as eluent) to give 3.48 g. This was taken up in 17 ml ether and stirred, giving 2.63 g of crystals after drying under high vacuum at 78° C., mp 138°–139° C.

$^1$H NMR (CDCl$_3$) δ 2.27 (s, 3H), 2.37 (m, 4H), 2.9 (m, 4H), 3.51 (s, 3H), 3.53 (s, 3H), 3.65 (m, 4H), 3.93 (ABq, J=15 Hz, 2H), 5.96 (s, 1H), 6.97 (t, 1H), 7.2 (m, 7), 8.02 (br. s, 1H). Anal. Calcd for $C_{30}H_{33}Cl_2N_3O_5$: C, 61.43; H, 5.67; N, 7.16. Found: C, 61.25; H, 5.60; N, 7.11.

Example 16

Dimethyl 4-(2,6-dichlorophenyl)-6-(4-methoxyphenyl)sulfinylmethyl-2-(4-methyl-1-piperazinyl)carbonylmethyl-1,4-dihydropyridine-3,5-dicarboxylate To a stirred solution of dimethyl 4-(2,6-dichlorophenyl)-6-(4-methoxyphenyl)thiomethyl-2-(4-methyl-1-piperazinyl)cabonylmethyl-1,4-dihydropyridine-3,5-dicarboxylate (1.01 g, 1.59 mmol) in ethyl acetate(10 ml) was added m-chloroperoxybenzoic acid (0.432 g, 2.07 mmol) in one portion at 0° C. and stirred at room temperature for 16 h. The reaction mixture was diluted with ethyl acetate (50 ml) and water (50 ml) followed by addition of $NaHSO_3$ aqueous solution (130 mg included in water). After 10 min stirring, the pH was adjusted to 9.0 with NaOH solution. The organic layer separated was washed twice with water and brine, dried over $Na_2SO_4$, and concentrated to afford 623 mg of crude product. TLC shows major spot at Rf 0.35 (dichloromethane methanol: 22/3). This crude product was chromatographed on 40 g silica gel (dichloromethane/methanol: 21/4 as eluent) to yield 296 mg which was crystallized from dichloromethane-isopropyl ether. $^1$H NMR data showed that this was a mixture of R and S sulfoxide isomers.

$^1$H NMR (DMSO-d$_6$) δ 2.19 and 2.21 (each s, 3H), 2.26 and 2.33 (each m, 4H), 3.37 (H$_2$O peak), 3.46 and 3.48 (each s, 6H), 3.81 and 3.82 (each s, 3H), 4.02 and 4.20 (each ABq's, J=12.3 Hz, v=186, J=11.4 Hz, v=195, 2H); two additional sets of ABq's are present, but partially obscured by the H$_2$O peak (J=15.6 Hz, J=15.9 Hz), 5.76 and 5.90 (each s, 1H), 7.15 (m, 1H), 7.16 (d, J=8.7 Hz, 2H), 7.32 and 7.35 (each d, J=15 Hz, 2H), 7.65 (d, J=8.7 Hz, 2H), 9.22 and 9.3 (each br. s, 1H).

Example 17

Dimethyl 4-(2,6-dichlorophenyl)-6-(4-methoxyphenyl)sulfonylmethyl-2-(4-methyl-1-piperazinyl)carbonylmethyl-1,4-dihydropyridine-3,5-dicarboxylate To a stirred solution of dimethyl 4-(2,6-dichlorophenyl)-6-(4-methoxyphenyl)thiomethyl-2-(4-methyl-1-piperazinyl)cabonylmethyl-1,4-dihydropyridine-3,5-dicarboxylate (1.01 g, 1.59 mmol) in ethyl acetate(15 ml) was added m-chloroperoxybenzoic acid (0.432 g, 2.07 mmol) in one portion at 0° C. and stirred for 10 min, then additional m-chloroperoxybenzoic acid (0.432 g, 2.07 mmol) was added and stirred at room temperature for 16 h. The reaction mixture was diluted with ethyl acetate (50 ml) and water (50 ml) followed by addition of $NaHSO_3$ aqueous solution (260 mg included in water). After 10 min stirring, the pH was adjusted to 9.0 with NaOH solution. The organic layer separated was washed twice with water and brine, dried over $Na_2SO_4$, and concentrated to afford 795 mg of crude product. This was chromatographed on 50 g silica gel (dichloromethane/methanol: 22/3 as eluent) to yield 242 mg of title compound.

$^1$H NMR (CDCl$_3$) δ 2.25 (s, 3H), 2.38 (m, 4H), 3.31 (s, 3H), 3.48 (s, 3H), 3.61 (m, 4H), 3.83 (s, 3H), 3.95 (ABq, J=15.6 Hz, 2H), 4.72 (ABq, J=14 Hz, 2H), 5.88 (s, 1H), 6.95 (dd, J=7.4, 8.4 Hz, 1H); 7.18 (d, J=7.7 Hz, 2H), 7.41 (ABq, J=8.94 Hz, 4H), 8.22 (br. s, 1H).

Example 18

Dimethyl 2-(4-cyclopentyl-1-piperazinyl)carbonylmethyl-4-(2,6-dichlorophenyl)-6-methyl-1,4-dihydropyridine-3,5-dicarboxylate This was prepared according to the procedure of Example 2, as HCl salt, mp 185°–195° C. Anal. Calcd for $C_{27}H_{33}N_3O_5Cl_2.HCl.0.5H_2O$: C, 54.42; H, 5.92; N, 7.05. Found: C, 54.06; H, 5.91; N, 6.86.

Example 19

Dimethyl 2-[4-(bicyclo[3.3.0]octane-3-one-7-yl)-1-piperazinyl]carbonylmethyl-4-(2,6-dichlorophenyl)-6-methyl-1,4-dihydropyridine-3,5-dicarboxylate This was prepared according to the procedure of Example 2, as HCl salt, mp 145°–155° C. MS: 603 (M$^+$).

Example 20

Dimethyl 2-[4-(bicyclo[3.3.0]octane-3-ol-7-yl)-1-piperazinyl]carbonylmethyl4-(2,6-dichlorophenyl)-6-methyl-1,4-dihydropyridine-3,5-dicarboxylate This was prepared according to the procedure of Example 3, as HCl salt, mp 190°–200° C. Anal. Calcd for $C_{30}H_{37}N_3O_6Cl_2.HCl.1.5H_2O$: C, 53.78; H, 6.17; N, 6.27. Found: C, 53.95; H, 6.00; N, 6.33.

Example 21

Dimethyl 2-[4-(bicyclo[3.3.0]octane-3-amine-7-yl)-1-piperazinyl]carbonylmethyl-4-(2,6-dichlorophenyl)-6-methyl-1,4-dihydropyridine-3,5-dicarboxylate This was prepared according to the procedure of Example 4, as HCl salt, mp 260°–270° C.

Example 22
Dimethyl 2-{4-[bicyclo[3.3.0]octane-3-(4-morpholinyl)-7-yl]-1-piperazinyl}carbonyl-methyl-4-(2,6-dichlorophenyl)-6-methyl-1,4-dihydropyridine-3,5-dicarboxylate This was prepared according to the procedure of Example 4, as HCl salt, mp 223°–225° C. Anal. Calcd for $C_{34}H_{44}N_4O_6Cl_2 \cdot 2HCl \cdot 3H_2O$: C, 49.76; H, 6.63; N, 6.83. Found: C, 50.01; H, 6.38; N, 6.72.

Example 23
Dimethyl 4-(2,6-dichlorophenyl)-6-methyl-2-[4-(5-norbornen-2-yl)-1-piperazinyl]-carbonylmethyl-1,4-dihydropyridine-3,5-dicarboxylate This was prepared according to the procedure of Example 2, as HCl salt, mp 190°–195° C. Anal. Calcd for $C_{30}H_{35}N_3O_5Cl_2 \cdot HCl \cdot 0.5H_2O$: C, 56.83; H, 5.88; N, 6.63. Found: C, 56.82; H, 6.15; N, 6.45.

Example 24
Dimethyl 4-(2,6-dichlorophenyl)-2-[4-(2-indanyl)-1-piperazinyl]carbonylmethyl-6-methyl-1,4-dihydropyridine-3,5-dicarboxylate This was prepared according to the procedure of Example 2, as HCl salt, mp 190°–200° C. Anal. Calcd for $C_{27}H_{33}N_3O_5Cl_2 \cdot HCl \cdot 0.5H_2O$: C, 57.82; H, 5.48; N, 6.52. Found: C, 57.68; H, 5.62; N, 6.41.

Example 25
Dimethyl 2-[4-(bicyclo[3.2.1]octan-2-yl)-1-piperazinyl]carbonylmethyl-4-(2,6-dichlo-rophenyl)-6-methyl-1,4-dihydropyridine-3,5-dicarboxylate This was prepared according to the procedure of Example 2, as HCl salt, mp 197°–207° C. Anal. Calcd for $C_{30}H_{37}N_3O_5Cl_2 \cdot HCl \cdot 1.5H_2O$: C, 55.09; H, 6.32; N, 6.42. Found: C, 55.19; H, 5.94; N, 6.49.

Example 26
Dimethyl 4-(2,6-dichlorophenyl)-6-methyl-2-[4-(4-piperidinyl)-1-piperazinyl]carbonylmethyl-1,4-dihydropyridine-3,5-dicarboxylate This was prepared according to the procedure of Example 2, as a gum. FAB HRMS Calcd for $C_{27}H_{34}N_4O_5Cl_2$: 564.1901. Found: 564.1904.

Example 27
Dimethyl 2-[4-(1-t-butoxycarbonylpiperidin-4-yl)-1-piperazinyl]carbonylmethyl-4-(2,6-dichlorophenyl)-6-methyl-1,4-dihydropyridine-3,5-dicarboxylate This was prepared according to the procedure of Example 2, mp 75°–90° C. Anal. Calcd for $C_{32}H_{42}N_4O_7Cl_2 \cdot 0.5(CH_3CO_2H)$: C, 56.98; H, 6.38; N, 8.05. Found: C, 57.01; H, 6.60; N, 7.82.

Example 28
Dimethyl 2-[4-(8-azabicyclo[3.2.1]octan-3-yl)-1-piperazinyl]carbonylmethyl-4-(2,6-dichlorophenyl)-6-methyl-1,4-dihydropyridine-3,5-dicarboxylate This was prepared according to the procedure of Example 8, as 2HCl salt, mp 160°–170° C.

Example 29
Dimethyl 2-{4-[8-(1-chloroethoxycarbonyl)-8-azabicyclo[3.2.1]octan-3-yl]-1-piperazinyl}carbonylmethyl-4-(2,6-dichlorophenyl)-6-methyl-1,4-dihydropyridine-3,5-dicarboxylate This was prepared according to the procedure of Example 7 and Olofson (*J. Org. Chem.*, 1984, 49, 2081), as HCl salt, mp 135°–145° C. Anal. Calcd for $C_{32}H_{39}N_4O_7Cl_3 \cdot HCl$: C, 52.33; H, 5.49; N, 7.63. Found: C, 52.52; H, 5.13; N, 6.93.

Example 30
Dimethyl 4-(2,6-dichlorophenyl)-2-{4-[8-(2-methoxyphenylmethyl)-8-azabicyclo[3.2.1]octan-3-yl]-1-piperazinyl}carbonylmethyl-6-methyl-1,4-dihydropyridine-3,5-dicarboxylate This was prepared according to the procedure of Example 6, as HCl salt, mp 205°–213° C. Anal. Calcd for $C_{37}H_{44}N_4O_6Cl_2 \cdot 3HCl \cdot 0.5H_2O$: C, 53.33; H, 5.83; N, 6.75. Found: C, 53.66; H, 5.71; N, 6.76.

Example 31
Dimethyl 4-(2,6-dichlorophenyl)-2-{4-[8-(2,4-difluorophenylmethyl)-8-azabicyclo[3.2.1]octan-3-yl]-1-piperazinyl}carbonylmethyl-6-methyl)-1,4-dihydropyridine-3,5-dicarboxylate This was prepared according to the procedure of Example 6, mp 210°–215° C. Anal. Calcd for $C_{36}H_{40}N_4O_5Cl_2F_2 \cdot 2HCl \cdot 2H_2O$: C, 52.31; H, 5.61; N, 6.78. Found: C, 52.58; H, 5.56; N, 6.67.

Example 32
Dimethyl 2-{4-[8-(3-chlorophenylmethyl)-8-azabicyclo[3.2.1]octan-3-yl]-1-piperazinyl}carbonylmethyl-4-(2,6-dichlorophenyl)-6-methyl-1,4-dihydropyridine-3,5-dicarboxylate This was prepared according to the procedure of Example 6, mp 210°–216° C. Anal. Calcd for $C_{36}H_{41}N_4O_5Cl_3 \cdot 2HCl \cdot 1.5H_2O$: C, 53.00; H, 5.68; N, 6.87. Found: C, 53.10; H, 5.78; N, 6.81.

Example 33
Dimethyl 4-(2,6-dichlorophenyl)-6-methyl-2-{4-[8-(4-trifluoromethylphenylmethyl)-8-azabicyclo[3.2.1]octan3-yl]-1-piperazinyl}carbonylmethyl-1,4-dihydropyridine-3,5-dicarboxylate This was prepared according to the procedure of Example 6, mp 217°–220° C. Anal.Calcd for $C_{37}H_{41}N_4O_5Cl_2F_3 \cdot 2HCl \cdot 2H_2O$: C, 51.76; H, 5.52; N, 6.53. Found: C, 51.60; H, 5.60; N, 6.51.

Example 34
Dimethyl 4-(2,6-dichlorophenyl)-6-methyl-2-[4-(8-methyl-8-azabicyclo[3.2.1]octan-3-yl)-1-piperazinyl]carbonylmethyl-1,4-dihydropyridine-3,5-dicarboxylate This was prepared according to the procedure of Example 6, as an amorphous solid. FAB HRMS Calcd for $C_{30}H_{38}N_4O_5Cl_2$: 604.2175. Found: 604.2197.

Example 35
Dimethyl 2-[4-(3-benzyl-3-azabicyclo[3.2.1]octan-8-yl)-1-piperazinyl]carbonylmethyl-4-(2,6-dichlorophenyl)-6-methyl-1,4-dihydropyridine-3,5-dicarboxylate This was prepared according to the procedure of Example 6, mp 195°–209° C. Anal. Calcd for $C_{36}H_{42}N_4O_5Cl_2 \cdot 2HCl \cdot 2H_2O$: C, 54.69; H, 6.12; N, 7.09. Found: C, 54.35; H, 5.98; N, 6.97.

Example 36
Dimethyl 4-(2,6-dichlorophenyl)-2-(4-methyl-1-piperazinyl)carbonylmethyl-6-phenyl-sulfinylmethyl-1,4-dihydropyridine-3,5-dicarboxylate A. Methyl 2-(2,6-Dichlorophenylmethylidene)-3-oxo-4-phenylthiobutanoate To a stirred suspension of sodium hydride (8.0 g, 0.2 mol) in dimethylformamide (100 ml) was added thiophenol (10 ml, 0.1 mol) dropwise at 0° C. After hydrogen gas evolution was ceased, methyl 4-chloroacetoacetate (11.5 ml, 0.1 mol) was added dropwise to the reaction mixture at 0° C. and the reaction mixture was stirred at room temperature for 20 min. The reaction mixture was poured into water (300 ml) and extracted with ether. The extract was washed with brine, dried (MgSO$_4$) and concentrated to afford 23.77 g of methyl 4-phenylthioacetoacetate as an orange color oil. To this oil was added 2,6-dichlorobenzaldehyde (19.25 g 0.11 mol), acetic acid (1.20 g, 20 mmol), piperidine (0.43 g, 5 mmol) and benzene (150 ml). This mixture was refluxed with azeotropic removal of water for 3 h. After evaporation of the solvent, the residue was purified by column chromatography on silica gel (hexane/ethyl acetate: 10/1 as eluent) to give 15.22 (39.9%) of desired compound. This is a mixture of double bond E and Z isomers.

$^1$H NMR (CDCl$_3$) δ 3.64 (s, 2.25H), 3.82 (s, 0.75H), 4.02 (s, 0.5H), 4.12 (s, 1.5H), 7.17–7.40 (m, 8H), 7.66 (s, 0.75H), 7.72 (s, 0.25H). IR (neat): 1720, 1690 cm$^{-1}$.

B. Dimethyl 4-(2,6-dichlorophenyl)-2-methoxycarbonylmethyl-6-phenylthiomethyl-1,4-dihydropyridine-3,5-dicarboxylate A mixture of methyl 2-(2,6-dichlorophenylmethylidene)-3-oxo-4-phenylthiobutanoate (14.21 g, 39.9 mmol) and dimethyl 3-aminoglutaconate (6.44 g, 37.2 mmol) was heated at 120° C. for 13 h. After cooling down to room temperature, the reaction mixture was purified by column chromatography on silica gel (hexane/ethyl acetate: 4/1 as eluent) to afford 8.10 g (40.6%) of wine red color viscous oil.

$^1$H NMR (CDCl$_3$) δ 3.52 (s, 3H), 3.53 (s, 3H), 3.61 (d, J=16.5 Hz, 1H), 3.66 (s, 3H), 3.86 (d, J=16.5 Hz, 1H), 4.23 (d, J=16.5 Hz, 1H), 4.52 (d, J=16.5 Hz, 1H), 5.98 (s, 1H), 6.99 (dd, J=7.7, 8.4 Hz, 1H), 7.21–7.41 (m, 7H), 7.69 (br. s, 1H). IR (neat): 3350, 1740, 1700, 1650, 1625 cm$^{-1}$.

C. Dimethyl 4-(2,6-dichlorophenyl)-2-(4-methyl-1-piperazinyl)carbonylmethyl-6-phenylthiomethyl-1,4-dihydropyridine-3,5-dicarboxylate A mixture of dimethyl 4-(2,6-dichlorophenyl)-2-methoxycarbonylmethyl-6-phenylthio-methyl-1,4-dihydropyridine-3,5-dicarboxylate (4.15 g, 7.7 mmol) and 6N NaOH (2.7 ml, 16 mmol) in aqueous methanol (water/methanol: 3 ml/15 ml) was stirred at room temperature for 2 h. The reaction mixture was treated with 1N HCl (20 ml) and extracted with dichloromethane. The extract was washed with brine, dried (MgSO$_4$) and concentrated to afford 4.51 g of brown amorphous solid. To a stirred solution of this crude acid in dichloromethane (50 ml) was added N-methylpiperazine (1.16 g, 11.55 mmol) at room temperature. After 16 h stirring at room temperature, the reaction mixture was washed with water and brine, dried (MgSO$_4$) and concentrated to afford 4.58 g of brown color viscous oil, which was purified by column chromatography on silica gel (methanol/dichloromethane: 1/20 as eluent) to afford 3.10 g (66.6%) of brown color viscous oil.

$^1$H NMR (CDCl$_3$) δ 2.28 (s, 3H), 2.30–2.36 (m, 4H), 3.53 (s, 3H), 3.53 (s, 3H), 3H), 3.58–3.65 (m, 4H), 3.69 (d, J=15.0 Hz, 1H), 4.22 (d, J=16.0 Hz, 1H), 4.25 (d, J=14.7 Hz, 1H), 4.45 (d, J=16.1 Hz, 1H), 5.97 (s, 1H), 6.99 (dd, J=7.7, 8.1 Hz, 1H), 7.20–7.32 (m, 5H), 7.42–7.45 (m, 2H), 8.66 (br.s, 1H). IR (neat): 3360, 1730, 1695, 1630 cm$^{-1}$.

D. Dimethyl 4-(2,6-dichlorophenyl)-2-(4-methyl-1-piperazinyl)carbonylmethyl-6-phenylsulfinylmethyl-1,4-dihydropyridine-3,5-dicarboxylate To a stirred solution of dimethyl 4-(2,6-dichlorophenyl)-2-(4-methyl-1-piperazinyl)carbonylmethyl-6-phenylthiomethyl-1,4-dihydropyridine-3,5-dicarboxylate (3.10 g, 5.1 m mol) in ethyl acetate (30 ml) was added 3-chloroperoxybenzoic acid (70%, 1.63 g, 6.6 mmol) at 0° C. After 14 h stirring at 0° C. to room temperature, the reaction mixture was diluted with ethyl acetate (300 ml), washed with NaHSO$_3$ aqueous solution, 10% NaOH aqueous solution, water and brine. After dry (MgSO$_4$), the solvent was evaporated to give 2.64 g of yellow amorphous solid, which was purified by column chromatography on silica gel (methanol/dichloromethane: 1/10 as eluent) to provide 0.207 g of starting material and 0.982 g (31%) of desired product as a yellow solid, of which 1H NMR data indicated that this yellow solid was 1:1 mixture of diastereomer. This yellow solid was recrystallized from dichloromethane/isopropyl ether to give 0.765 g of yellow powder, which was washed with methanol to afford 0.404 g of pale yellow powder as single diastereomer, mp 226°–227°.

$^1$H NMR (CDCl$_3$) δ 2.31 (s, 3H), 2.38–2.46 (m, 4H), 3.53 (s, 3H), 3.53 (s, 3H), 3.60–3.70 (m, 4H), 3.85 (d, J=15.4 Hz, 1H), 3.88 (d, J=12.8 Hz, 1H), 3.96 (d, J=15.4 Hz, 1H), 4.53 (d, J=12.8 Hz), 5.98 (s, 1H), 7.02 (dd, J=7.7, 8.4 Hz, 1H), 7.25–7.28 (m, 2H), 7.49–7.58 (m, 3H), 7.74–7.78 (m, 2H), 8.14 (br. s, 1H). IR (nujol): 3250, 3200, 3100, 1710,1685, 1660, 1650, 1620 cm$^{-1}$. Anal. Calcd for C$_{29}$H$_{31}$Cl$_2$N$_3$O$_6$S: C, 56.13; H, 5.04; N, 6.77. Found: C, 55.91; H, 4.93; N, 6.79.

The filtrates of the above crystalline were combined and concentrated to give yellow solid which was recrystallized from ethyl acetate to give 0.124 g of yellow powder. This was 2:3 mixture of former compound and its diastereomer. The filtrate was concentrated to give yellow solid which was recrystallized from dichloromethane/ether to afford 0.172 g of another diastereomer as an yellow powder.

mp 129°–131°; $^1$H NMR (CDCl$_3$) δ 2.37 (s, 3H), 2.40–2.65 (m, 4H), 3.37 (d, J=12.8 Hz, 1H), 3.56 (s, 3H), 3.60 (s, 3H), 3.60–3.85 (m, 5H), 4.25 (br.d, J=15.4 Hz, 1H), 4.98 (d, J=12.5 Hz, 1H), 6.07 (s, 1H), 7.01 (dd, J=7.3, 8.4 Hz, !H), 7.24 (d, J=7.7 Hz, 2H), 7.50–7.58 (m, 3H), 7.76–7.79 (m, 2H), 8.19 (br.s, 1H). IR (nujol): 3300, 3240, 3200, 3100, 1705, 1695, 1655, 1625 cm$^{-1}$. Anal. Calcd for C$_{29}$H$_{31}$Cl$_2$N$_3$O$_6$S.2.5H$_2$O: C, 52,33; H, 5.45; N, 6.31. Found: C, 52,42; H, 5.00; N, 6.26.

The title compounds of Example 37–41 were prepared by a procedure similar to that described in Example 36, as HCl salt except for Example 40 and 41.

Example 37

Dimethyl 4-(2,6-dichlorophenyl)-6-(2-methoxyphenyl)sulfinylmethyl-2-(4-methyl-1-piperazinyl)carbonylmethyl-1,4-dihydropyridine-3,5-dicarboxylate Yellow solid. mp 160°; $^1$H NMR (free base, CDCl$_3$) δ 2.33 (s, 3H), 2.40–2.50 (m, 4H), 3.60–4.00 (m, 6H), 3.46 (s, 3H), 3.51 (s, 3H), 3.90 (s, 3H), 4.36 (d, J=13.2 Hz, 1H), 4.51 (d, J=13.2 Hz, 1), 5.90 (s, 1H), 6.85–7.10 (m, 2H), 7.15–7.40 (m, 3H), 7.47 (m, 1H), 7.82 (m, 1H), 8.14 (br. s, 1H). IR (KBr): 3420, 1695, 1645 cm$^{-1}$. Anal. Calcd for C$_{30}$H$_{33}$N$_3$O$_7$SCl$_2$. HCl.3H$_2$O: C, 48.62; H, 5.44; N, 5.67; S, 4.44; Cl, 14.35. Found: C, 49.00; H, 5.55; N, 5.51; S, 4.31; Cl, 14.53.

Example 38

Dimethyl 4-(2,6-dichlorophenyl)-2-(4-methyl-1-piperazinyl)carbonylmethyl-6-(2-tolyl)sulfinylmethyl-1,4-dihydropyridine-3,5-dicarboxylate Yellow solid, mp 183°; $^1$H NMR (free base, CDCl$_3$) δ 2.33 (s, 3H), 2.45 (s, 3H), 2.40–2.55 (m, 4H), 3.46 (s, 3H), 3.53 (s, 3H), 3.60–3.80 (m, 4H), 3.87 (d, J=15.8 Hz, 1H), 3.94 (d, J=13.0 Hz, 1H), 3.99 (d, J=15.8 Hz, 1H), 4.55 (d, J=12.8 Hz, 1H), 5.94 (s, 1H), 7.02 (t, J=7.3 Hz, 1H), 7.15–7.30 (m, 3H), 7.35–7.50 (m, 2H), 7.96 (d, J=7.7 Hz, 1H), 8.05 (br. s, 1H). IR (KBr): 3450, 1690, 1650, 1625 cm$^{-1}$. Anal. Calcd for $C_{30}H_{33}Cl_2N_3O_6S \cdot HCl \cdot 1.5H_2O$: C, 51.62; H, 5.34; N, 6.02; S, 4.59; Cl, 15.24. Found: C, 51.61; H, 5.73; N, 6.06; s, 4.57; Cl, 15.64.

Example 39

Dimethyl 6-(2-chlorophenyl)sulfinylmethyl-4-(2,6-dichlorophenyl)-2-(4-methyl-1-piperazinyl) carbonylmethyl-1,4-dihydropyridine-3,5-dicarboxylate Yellow solid, mp 180°–181° C.; $^1$H NMR (free base, CDCl$_3$) δ 2.32 (s, 3H), 2.35–2.50 (m, 4H), 3.46 (s, 3H), 3.53 (s, 3H), 3.60–3.75 (m, 4H), 3.91 (d, J=15.4 Hz, 1H), 3.99 (d, J=15.4 Hz, 1H), 4.42 (d, J=13.4 Hz, 1H), 4.48 (d, J=13.4 Hz, 1H), 5.91 (s, 1H), 7.00 (t, J=8.1 Hz, 1H), 7.24 (d, J=8.1 Hz, 2H), 7.38 (dd, J=1.1, 7.9 Hz, 1H), 7.47 (dt, J=1.8, 7.9 Hz, 1H), 7.58 (dt, J=1.1, 7.3 Hz, 1H), 8.00 (dd, J=1.5, 7.7 Hz, 1H), 8.18 (br. s, 1H). IR (KBr): 3450, 1695, 1650 cm$^{-1}$. Anal. Calcd for $C_{29}H_{30}Cl_3N_3O_6S \cdot HCl \cdot 1.5H_2O$: C, 48.48; H, 4.77; N, 5.85; S, 4.46; Cl, 19.74. Found: C, 48.41; H, 4.92; N, 5.84; S, 4.40; Cl, 19.74.

Example 40

Dimethyl 4-(2,6-dichlorophenyl)-2-(4-methyl-1-piperazinyl)carbonylmethyl-6-(2-pyridyl)sulfinylmethyl-1,4-dihydropyridine-3,5-dicarboxylate Yellow powder, mp 207°–210° C. (dec); $^1$H NMR (CDCl$_3$) δ 2.38 (s, 3H), 2.53 (br.s, 4H), 3.53 (s, 3H), 3.55 (s, 3H), 3.7 (br. s, 4H), 3.95 (br. s, 2H), 4.25 (d, J=13.2 Hz, 1H), 4.69 (d, J=13.6 Hz, 1H), 5.97 (s, 1H), 7.01 (dd, J=7.7, 8.4 Hz, 1H), 7.26 (d, J=7.7 Hz, 2H), 7.39–7.44 (m, 1H), 7.95–8.07 (m, 2H), 8.30 (br.s, 1H), 8.69–8.71 (m, 1H). IR (nujol): 3250, 3200, 3100, 1710, 1700, 1680, 1670, 1655, 1650 cm$^{-1}$. Anal. Calcd for $C_{28}H_{30}Cl_2N_4O_6S \cdot 0.5H_2O$: C, 53.34; H, 4.96; N, 8.89; Cl, 11.25; S; 5.08. Found: C, 53.09; H, 4.81; N, 8.74; Cl, 11.34; S, 5.11.

Example 41

Dimethyl 4-(2,6-dichlorophenyl)-2-(4-methyl-1-piperazinyl)carbonylmethyl-6-methylsulfinylmethyl-1,4-dihydropyridine-3,5-dicarboxylate Yellow prism, mp 209°–210° C.; $^1$H NMR (CDCl$_3$) δ 2.31 (s, 3H), 2.35–2.45 (m, 4H), 2.73 (s, 3H), 3.53 (s, 6H), 3.55–3.70 (m, 4H), 3.71 (d, J=15.8 Hz, 1H), 4.04 (d, J=13.2 Hz, 1H), 4.14 (d, J=15.8 Hz, 1H), 4.39 (d, J=13.2 Hz, 1H), 6.05 (s, 1H), 7.02 (dd, J=7.3, 8.4 Hz, 1H), 7.27 (d, J=8.1Hz, 2H), 8.47 (br. s, 1H). IR (nujol): 3250, 3190, 3080, 1700, 1680, 1640, 1620 cm$^{-1}$. Anal. Calcd for $C_{24}H_{29}Cl_2N_3O_6S$: C, 51.62; H, 5.23; N, 7.52; Cl, 12.70; S, 5.74. Found: C, 51.65; H, 5.35; N, 7.43; Cl, 12.55; S, 5.83.

Example 42

Dimethyl 4-(2,6-dichlorophenyl)-6-[2-(5-isopropyl-2-methoxyphenyl)ethyl]-2-[4-(4-pyridyl)methyl-1-piperazinyl]carbonylmethyl-1,4-dihydropyridine-3,5-dicarboxylate A. Methyl 5-(5-isopropyl-2-methoxyphenyl)-3-oxopentanoate To a stirred suspension of sodium hydride (60% oil suspension, 0.44 g,11 mmol) in THF (25 ml) was added methyl acetoacetate (1.08 ml, 10 mmol) dropwise at 0° C. After 10 min stirring at 0° C., n-buthyllithium (1.31M in hexane, 8 ml, 10.5 mmol) was added to the reaction mixture at 0° C. To this orange color solution was added a solution of 5-isopropyl-2-methoxybenzyl chloride (1.99 9, 10 mmol) in THF (5 ml) at 0° C. After 40 min stirring at 0° C. to room temperature, the reaction mixture was poured into 1N HCl (20 ml) and extracted with ethyl acetate. The extract combined was dried (MgSO$_4$) and concentrated to give 3.02 g of yellow oil, which was purified by column chromatography on silica gel (hexane/ethyl acetate: 10/1 as eluent) to afford 1.55 g (55.8%) of title compound as yellow oil.

$^1$H NMR (CDCl$_3$) δ 1.21 (d, J=7.0 Hz, 6H), 2.80–2.91 (m, 5H), 3.45 (s, 2H), 3.72 (s, 3H), 3.79 (s, 3H), 6.77 (d, J=8.1 Hz, 1H), 6.98 (d, J=2.2 Hz, 1H), 7.04 (dd, J=2.2, 8.4 Hz, 1H). IR (neat): 1750, 1720 cm$^{-1}$.

B. Dimethyl 4-(2,6-dichlorophenyl)-6-[2-(5-isopropyl-2-methbxyphenyl)ethyl]-2-methoxycarbonylmethyl-1,4-dihydropyridine-3,5-dicarboxylate A mixture of methyl 5-(5-isopropyl-2-methoxyphenyl)-3-oxopentanoate (7.04 g, 25 mmol), 2,6-dichlorobenzaldehyde (4.38 g, 25 mmol), piperidine (0.20 g, 2.3 mmol), and acetic acid (0.60 g, 10 mmol) in benzene (50 ml) was refluxed with azeotropic removal of water for 2 h. The reaction mixture was concentrated and purified by column chromatography on silica gel (hexane/ethyl acetate: 10/1 as eluent) to give 6.70 g(61.6%) of orange color viscous oil. To this oil (6.70 g, 15.4 mmol) was added dimethyl 3-aminoglutaconate (2.42 g, 14 mmol) and the mixture was stirred at 120° C. for 22 h. The reaction mixture was cooled down to room temperature and purified by column chromatography on silica gel (hexane/ethyl acetate: 4/1 as eluent) to afford 2.23 g (27%) of title compound as yellow solid, mp162°–163°.

$^1$H NMR (CDCl$_3$) δ 1.21 (d, J=7.0 Hz, 6H), 2.81–2.94 (m, 5H), 3.53 (s, 3H), 3.56 (s,3H), 3.72 (s, 2H), 3.73 (s, 3H), 3.88 (s, 3H), 5.98 (s, 1H), 6.80 (d, J=9.2 Hz, 1H), 6.87 (br. s, 1H), 6.99 (t, J=8.1 Hz, 1H), 7.05 (d, J=2.2 Hz, 1H), 7.05 (dd, J=2.6, 9.2 Hz, 1H), 7.24 (d, J=8.1 Hz, 2H). IR (neat): 3350, 1740, 1690, 1650 cm$^{-1}$. Anal. Calcd for $C_{30}H_{33}Cl_2NO_7$: C, 61.02; H, 5.63; N, 2.37; Cl, 12.01. Found: C, 60.84; H, 5.68; N, 2.36; Cl, 11.75.

C. 4-Picolylpiperazine

A mixture of benzyloxycarbonylpiperazine (2.20 g, 10 mmol),4-chloromethylpyridine hydrochloride (1.64 g, 10 mmol), and triethylamine (2.8 ml, 20 mmol) in ethanol (40 ml) was refluxed for 20 h. After evaporation of the solvent, the residue was diluted with water, extracted with dichloromethane, dried (MgSO$_4$) and concentrated to give 2.53 g of brown viscous oil. This oil was purified by column chromatography on silica gel (methanol/dichloromethane: 1/10) to afford 1.47 g (49.2%) of brown viscous oil. This oil was hydrogenated (10% Pd/C; 0.15 g, methanol; 30 ml, room temperature for 12 h) to give 0.78 g (91.8%) of yellow viscous oil.

$^1$H NMR (CDCl$_3$) δ 2.05 (br. s, 1H), 2.42 (t, J=4.8 Hz, 4H), 2.90 (t, J=4.8 Hz, 4H), 3.49 (s, 2H), 7.27 (d, J=5.1 Hz, 2H), 8.53 (dd, J=1.8, 4.4 Hz, 2H). IR (neat): 3280 cm$^{-1}$.

D. Dimethyl 4-(2,6-dichlorophenyl)-6-[2-(5-isopropyl-2-methoxyphenyl)ethyl]-2-[4-(4-pyridyl)methyl-1-piperazinyl]carbonylmethyl-1,4-dihydropyridine-3,5-dicarboxylate To a stirred solution of dimethyl 4-(2,6-dichlorophenyl)-6-[2-(5-isopropyl-2-methoxy-phenyl)ethyl]-1,4-dihydropyridine-3,5-dicarboxylate (295 mg, 0.5 mmol) in dioxane (2.5 ml) was added 2N NaOH aqueous solution (0.5 ml, 1 mmol) at room temperature. After 2 h stirring, the reaction mixture was acidified with 1N HCl (2 ml, 2 mmol) and extracted with dichloromethane. The extract was dried (MgSO$_4$) and concentrated to 10 ml solution. To this solution was added 4-picolylpiperazine (106 mg, 0.6 mmol) followed by addition of 1-ethyl-3-(3-dimethylaminopropyl) carbodiimide hydrochloride (115 mg, 0.6 mmol) at room temperature. After 18 h stirring, the reaction mixture was washed with water and brine, dried (MgSO$_4$) and concentrated to give 0.45 g of yellow amorphous solid. This was purified by column chromatography on silica gel (methanol/dichloromethane: 1/40 as eluent) to afford 0.26 g (70.5%) of pale yellow viscous oil. To this free amine was added HCl saturated methanol (5 ml) and the resulting pale yellow solution was concentrated to give 262 mg (50.7%) of yellow powder, mp 133°–138°.

$^1$H NMR (free base, CDCl$_3$) δ 1.20 (d, J=7.0 Hz, 6H), 2.35–2.50 (m, 4H), 2.75–3.00 (m, 5H), 3.50 (s, 2H), 3.52 (s, 3H), 3.55 (d, J=14.7 Hz, 1H), 3.56 (s, 3H), 3.63–3.70 (m, 4H), 3.90 (s, 3H), 4.27 (d, J=14.7 Hz, 1H), 5.99 (s, 1H), 6.79 (d, J=8.8 Hz, 1H), 6.97–7.05 (m, 3H), 7.23–7.26 (m, 4H), 7.76 (br. s, 1H), 8.50–8.60 (m, 2H). IR (nujol): 1690, 1640 cm$^{-1}$. Anal. Calcd for C$_{39}$H$_{44}$Cl$_2$N$_4$O$_6$.2HCl.3H$_2$O: C, 54.30; H, 6.08; N, 6.49; Cl, 16.44. Found: C, 54.52; H, 5.79; N, 6.52; Cl, 16.46.

The title compounds of Example 46–56 were prepared by a procedure similar to that described in Example 45, as HCl salt.

Example 43

Dimethyl 4-(2,6-dibromophenyl)-6-(2-phenylethyl)-2-(4-pyrrolidinylcarbonylmethyl-1-piperazinyl)carbonylmethyl-1,4-dihydropyridine-3,5-dicarboxylate mp 149.5°–150.5° C. $^1$H NMR (free base, CDCl$_3$) δ 1.82–1.97 (m, 4H), 2.51–2.62 (m, 4H), 2.83–2.98 (m, 4H), 3.14 (s, 2H), 3.42–3.50 (m, 4H), 3.52 (s, 3H), 3.54 (s, 3H), 3.64–3.75 (m, 5H), 4.20 (d, J=15.0 Hz, 1H), 5.98 (s, 1H), 6.84 (m, 4H), 7.19 (t, J=7.7 Hz, 2H), 7.51 (d, J=7.7 Hz, 2H), 7.96 (s, 1H).

Example 44

Dimethyl 4-(2,6-dichlorophenyl)-2-(4-methyl-1-piperazinyl)carbonylmethyl-6-[2-(2-pyridyl)ethyl]-1,4-dihydropyridine-3,5-dicarboxylate mp 84°–86° C.

$^1$H NMR (CDCl$_3$) δ 2.29 (s, 3H), 2.31–2.45 (m, 4H), 3.02–3.47 (m, 4H), 3.53 (s, 3H), 3.55 (s, 3H), 3.59–3.69 (m, 4H), 3.85 (d, J=14.7 Hz, 1H), 4.06 (d, J=14.7 Hz, 1H), 6.00 (s, 1H), 6.99 (t, J=7.9 Hz, 1H), 7.12 (dd, J=4.7, 7.7 Hz, 1H), 7.23 (d, J=7.7 Hz, 1H), 7.23 (d, J=8.1 Hz, 2H), 7.59 (t, J=7.7 Hz, 1H), 8.61 (d, J=4.7 Hz, 1H), 8.67 (s, 1H). IR (KBr): 3300, 1695, 1625 cm$^{-1}$. Anal. Calcd for C$_{29}$H$_{33}$Cl$_2$N$_4$O$_5$.2H$_2$O: C, 55.70; H, 5.97; N, 8.97. Found: C, 55.80; H, 5.61; N, 9.05.

Example 45

Dimethyl 4-(2,6-dichlorophenyl)-2-(4-methyl-1-piperazinyl)carbonylmethyl-6-[2-(2-thienyl)ethyl]-1,4-dihydropyridine-3,5-dicarboxylate mp 142°–145° C.; $^1$H NMR (free base, CDCl$_3$) δ 2.28 (s, 3H), 2.38 (br. s, 4H), 2.86–3.16 (m, 4H), 3.54 (s, 3H), 3.56 (s, 3H), 3.66 (m, 4H), 3.75 (d, J=15.0 Hz, 1H), 4.18 (d, J=15.0 Hz, 1H), 5.99 (s, 1H), 6.87 (d, J=3.3 Hz, 1H), 6.92 (dd, J=3.3, 4.8 Hz, 1H), 7.00 (t, J=7.9 Hz, 1H), 7.12 (d, J=4.8 Hz, 1H), 7.23 (s, 1H), 7.25 (d, J=7.9 Hz, 2H), 8.02 (br. s, 1H). IR (KBr): 3450, 1695, 1650 cm$^{-1}$. Anal. Calcd for C$_{28}$H$_{32}$Cl$_2$N$_3$O$_5$S.HCl.2.5H$_2$O: C, 49.89; H, 5.53; N, 6.23. Found: C, 49.38; H, 5.16; N, 6.41.

Example 46

Dimethyl 4-(2,6-dichlorophenyl)-6-[2-(2-methoxyphenyl)ethyl]-2-[4-(4-pyridylmethyl)-1-piperazinyl]carbonylmethyl-1,4-dihydropyridine-3,5-dicarboxylate mp 160°–162° C. (dec); $^1$H NMR (free base, CDCl$_3$) δ 2.35–2.55 (m, 4H), 2.80–3.00 (m, 4H), 3.51 (s, 2H), 3.52 (s, 3H), 3.56 (s, 3H), 3.60–3.75 (m, 5H), 3.92 (s, 3H), 4.27 (d, J=14.7 Hz, 1H), 5.98 (s, 1H), 6.80–6.95 (m, 2H), 7.00 (t, J=8.1 Hz, 1H), 7.15–7.30 (m, 6H), 7.82 (s, 1H), 8.54 (d, J=5.1 Hz, 2H). IR (KBr): 3400, 2950, 2550, 1690, 1640 cm$^{-1}$. Anal. Calcd for C$_{36}$H$_{38}$Cl$_2$N$_4$O$_6$.2HCl.1.5H$_2$O: C, 54.49; H, 5.46; N, 7.06; Cl, 17.87. Found: C, 54.61; H, 5.60; N, 7.11; Cl, 17.48.

Example 47

Dimethyl 4-(2,6-dichlorophenyl)-6-[2-(2-methoxyphenyl)ethyl]-2-(4-pyrrolidinylcarbonylmethyl-1-piperazinyl)carbonylmethyl-1,4-dihydropyridine-3,5-dicarboxylate mp 157.5°–158.9° C. (dec); $^1$H NMR (free base, CDCl$_3$) δ 1.80–2.00 (m, 4H), 2.45–2.65 (m, 4H), 2.75–3.00 (m, 4H), 3.13 (s, 2H), 3.40–3.55 (m, 4H), 3.53 (s, 3H), 3.56 (s, 3H), 3.60–3.75 (m, 5H), 3.92 (s, 3H), 4.24 (d, J=15.0 Hz, 1H), 5.98 (s, 1H), 6.80–6.90 (m, 2H), 6.99 (t, J=7.92 Hz, 1H), 7.30–7.40 (m, 4H), 7.85 (s, 1H). IR (KBr): 3450, 2950, 1690, 1650 cm$^{-1}$. Anal. Calcd for C$_{36}$H$_{42}$Cl$_2$N$_4$O$_7$.HCl.2.5H$_2$O: C, 54.44; H, 5.98; N, 7.05; Cl, 13.39. Found: C, 54.37; H, 5.87; N, 7.00; Cl, 13.89.

Example 48

Dimethyl 4-(2,6-dichlorophenyl)-6-[2-(2-methoxyphenyl)ethyl]-2-[4-(3-pyridylmethyl)-1-piperazinyl]carbonylmethyl-1,4-dihydropyridine-3,5-dicarboxylate mp 159°–161° C. (dec); $^1$H NMR (free base, CDCl$_3$) δ 2.40–2.50 (m, 4H), 2.75–3.00 (m, 4H), 3.52 (s, 6H), 3.56 (s, 2H), 3.60–3.75 (m, 3H), 3.92 (s, 3H), 4.27 (d, J=15.0 Hz, 1H), 5.98 (s, 1H), 6.80–6.95 (m, 2H), 7.00 (t, J=7.9 Hz, 1H), 7.15–7.35 (m, 5H), 7.65 (d, J=7.7 Hz, 1H), 7.83 (s, 1H), 8.53 (br. s, 2H). IR (KBr): 3400, 2950, 2550, 1690, 1650 cm$^{-1}$. Anal. Calcd for C$_{36}$H$_{38}$Cl$_2$N$_4$O$_6$.2HCl.4H$_2$O: C, 51.56; H, 5.77; N, 6.68; Cl, 16.91. Found: C, 51.65; H, 5.60; N, 6.73; Cl, 17.00.

Example 49

Dimethyl 4-(2,6-dichlorophenyl)-6-[2-(2-methoxyphenyl)ethyl]-2-[4-(2-pyridylmethyl)-1-piperazinyl]carbonylmethyl-1,4-dihydropyridine-3,5-dicarboxylate mp 154°–155° C. (dec); $^1$H NMR (free base, CDCl$_3$) δ 2.40–2.60 (m, 4H), 2.75–3.00 (m, 4H), 3.52 (s, 3H), 3.56 (s, 3H), 3.67 (s, 2H), 3.60–3.75 (m, 5H), 3.92 (s, 3H), 4.28 (d, J=15.0 Hz, 1H), 5.98 (s, 1H), 6.80–6.95 (m, 2H), 6.99 (t, J=8.1 Hz, 1H), 7.15–7.40 (m, 5H), 7.37 (d, J=7.7 Hz, 1H), 7.65 (dt, J=1.8, 7.7 Hz, 1H), 7.87 (s, 1H), 8.57 (d, J=4.8 Hz, 1H). IR (KBr): 3420, 2950, 2550, 1690, 1650 cm$^{-1}$. Anal. Calcd for C$_{36}$H$_{38}$Cl$_2$N$_4$O$_6$.2HCl.3H$_2$O: C, 52.69; H, 5.65; N, 6.83; Cl, 17.28. Found: C, 52.73; H, 5.91; N, 6.73; Cl, 16.90.

Example 50

Dimethyl 4-(2,6-dichlorophenyl)-6-(2-phenylethyl)-2-(4-pyrrolidinylcarbonylmethyl-1-piperazinyl)carbonylmethyl-1,4-dihydropyridine-3,5-dicarboxylate mp 180°–184° C.; $^1$H NMR (free base, CDCl$_3$) δ 1.80–2.00 (m, 4H), 2.57 (m, 4H), 2.80–3.00 (m, 4H), 3.13 (s, 2H), 3.46 (q like, J=7.0 Hz, 4H), 3.54 (s, 3H), 3.56 (s, 2H), 3.70 (m, 4H), 3.76 (d, J=15.0 Hz, 1H), 4.16 (d, J=15.0 Hz, 1H), 5.99 (s, 1H), 7.00 (dd, J=8.3, 8.4 Hz, 1H), 7.15–7.30 (m, 7H), 7.98 (s, 1H). IR (KBr): 3430, 1690, 1655 cm$^{-1}$. Anal. Calcd for C$_{35}$H$_{40}$Cl$_2$N$_4$O$_6$.HCl.3H$_2$O: C, 54.30; H, 6.12; N, 7.24; Cl, 13.74. Found: C, 54.29; H, 5.75; N, 7.18; Cl, 13.73.

Example 51

Dimethyl 4-(2,6-dichlorophenyl)-2-(4-isopropylaminocarbonylmethyl-1-piperazinyl)

carbonylmethyl-6-[2-(2-methoxyphenyl)ethyl]-1,4-dihydropyridine-3,5-dicarboxylate mp 161°–163° C.; $^1$H NMR (free base, CDCl$_3$) δ 1.15 (s, 3H), 1.18 (s, 3H), 2.40–2.60 (m, 4H), 2.75–3.00 (m, 4H), 2.98 (s, 2H), 2.99 (s, 2H), 3.54 (s, 3H), 3.56 (s, 3H), 3.50–3.90 (m, 5H), 3.93 (s, 3H), 4.01–4.20 (m, 1H), 4.33 (d, J=14.7 Hz, 1H), 5.99 (s, 1H), 6.78 (m, 1H), 6.85–6.95 (m, 2H), 7.00 (t, J=8.1 Hz, 1H), 7.15–7.35 (m, 4H), 7.78 (s, 1H). IR (KBr): 3420, 1690 cm$^{-1}$. Anal. Calcd for C$_{35}$H$_{42}$Cl$_2$N$_4$O$_7$.HCl.2H$_2$O: C, 54.30; H, 6.12; N, 7.24; Cl, 13.74. Found: C, 54.32; H, 6.54; N, 7.24; Cl, 13.98.

Example 52

Dimethyl 4-(2,6-dichlorophenyl)-2-[4-(2-hydroxyethyl)-1-piperazinyl]carbonylmethyl-6-[2-(2-methoxyphenyl)ethyl]-1,4-dihydropyridine-3,5-dicarboxylate mp 225°–227° C.; $^1$H NMR (free base, CDCl$_3$) δ 2.35–2.60 (m, 8H), 2.75–3.00 (m, 4H), 3.54 (s, 3H), 3.56 (s, 3H), 3.60–3.75 (m, 5H), 3.93 (s, 3H), 4.29 (d, J=15.0 Hz, 1H), 5.99 (s, 1H), 6.80–6.90 (m, 2H), 7.00 (t, J=7.9 Hz, 1H), 7.15–7.35 (m, 4H), 7.83 (s, 1H). IR (KBr): 3450, 1690 cm$^{-1}$. Anal. Calcd for C$_{32}$H$_{37}$Cl$_2$N$_3$O$_7$.HCl.1.5H$_2$O: C, 54.13; H, 5.82; N, 5.92; Cl, 14.98. Found: C, 54.01; H, 6.02; N, 5.83; Cl, 15.05.

Example 53

Dimethyl 4-(2,6-dichlorophenyl)-6-[2-(2-methoxyphenyl)ethyl]-2-[4-(2-pyrimidyl)-1-piperazinyl]carbonylmethyl-1,4-dihydropyridine-3,5-dicarboxylate mp 129°–131° C. (dec); $^1$H NMR (free base, CDCl$_3$) δ 2.75–3.00 (m, 4H), 3.55 (s, 6H), 3.64 (d, J=14.7 Hz, 1H), 3.70–3.90 (m, 8H), 3.94 (s, 3H), 4.36 (d, J=14.7 Hz, 1H), 5.99 (s, 1H), 6.53 (t, J=4.8 Hz, 1H), 6.80–6.95 (m, 2H), 6.98 (t, J=8.1 Hz, 1H), 7.15–7.35 (m, 4H), 7.76 (s, 1H), 8.32 (d, J=4.8 Hz, 2H). IR (KBr): 3450, 2950, 1700, 1630 cm$^{-1}$.

Example 54

Dimethyl 4-(2,6-dichlorophenyl)-6-[2-(2-methoxyphenyl)ethyl]-2-[4-(1-methyl-4-piperidinyl)-1-piperazinyl]carbonylmethyl-1,4-dihydropyridine-3,5-dicarboxylate This was prepared according to the procedure of Example 6, as HCl salt, mp 188°–190° C. (dec).

$^1$H NMR (free base, CDCl$_3$) δ 1.45–1.80 (m, 5H), 1.85–2.05 (m, 2H), 2.27 (s, 3H), 2.40–2.60 (m, 4H), 2.75–3.00 (m, 6H), 3.54 (s, 3H), 3.55 (s, 3H), 3.50–3.65 (m, 5H), 3.92 (s, 3H), 4.28 (d, J=14.7 Hz, 1H), 5.98 (s, 1H), 6.80–6.90 (m, 2H), 6.99 (t, J=8.1 Hz, 1H), 7.15–7.35 (m, 4H), 7.92 (s, 1H). IR (KBr): 3450, 1690, 1650 cm$^{-1}$ Anal. Calcd for C$_{36}$H$_{44}$Cl$_2$N$_4$O$_6$.2HCl.H$_2$O: C, 54.69; H, 6.12; N, 7.09; Cl, 17.94. Found: C, 54.89; H, 6.58; N, 7.30; Cl, 18.23.

Example 55

Dimethyl 4-(2,6-dichlorophenyl)-6-[2-(2-methoxyphenyl)ethyl]-2-[4-(8-methyl-8-azabicyclo[3.2.1]octan-3-yl)-1-piperazinyl]carbonylmethyl-1,4-dihydropyridine-3,5-dicarboxylate This was prepared according to the procedure of Example 10, as HCl salt, mp 206°–208° C. (dec).

$^1$H NMR (free base, CDCl$_3$) δ 1.45–1.65 (m, 4H), 1.70–1.90 (m, 2H), 2.00–2.15 (m, 2H), 2.35 (s, 3H), 2.40–2.70 (m, 5H), 2.75–3.00 (m, 4H), 3.30 (br. s, 2H), 3.54 (s, 3H), 3.55 (s, 3H), 3.60–3.70 (m, 5H), 3.92 (s, 3H), 4.26 (d, J=15.0 Hz, 1H), 5.98 (s, 1H), 6.75–6.90 (m, 2H), 6.99 (t, J=8.1 Hz, 1H), 7.10–7.35 (m, 4H), 7.91 (s, 1H). IR (KBr): 3420, 1690, 1645 cm$^{-1}$. Anal. Calcd for C$_{38}$H$_{46}$Cl$_2$N$_4$O$_6$.2HCl.2H$_2$O: C, 54.68; H, 6.28; N, 6.71; Cl, 16.99. Found: C, 54.64; H, 6.76; N, 6.65; Cl, 16.69.

Example 56

Dimethyl 4-(2,6-dichlorophenyl)-6-[2-(2-methoxyphenyl)ethyl]-2-[4-(3-quinuclidinyl)-1-piperazinyl]carbonylmethyl-1,4dihydropyridine-3,5-dicarboxylate This was prepared according to the procedure of Example 10, as HCl salt, mp 177.5°–178.9° C. (dec). $^1$H NMR (free base, CDCl$_3$) δ 0.80–0.95 (m, 1H), 1.35–1.55 (m, 1H), 1.65–2.15 (m, 6H), 2.25–2.50 (m, 4H), 2.60–3.10 (m, 8H), 3.60–3.75 (m, 5H), 3.93 (s, 3H), 4.26 (dd, J=4.6, 14.8 Hz, 1H), 5.99 (s, 1H), 6.80–6.95 (m, 2H), 7.00 (t, J=7.9 Hz, 1H), 7.15–7.35 (m, 4H), 7.86 (s, 1H). IR (KBr): 3450, 2950, 1690, 1650 cm$^{-1}$. Anal. Calcd for C$_{37}$H$_{44}$Cl$_2$N$_4$O$_6$.2HCl.3H$_2$O: C, 52.99; H, 6.25; N, 6.68; Cl, 16.91. Found: C, 53.19; H, 6.59; N, 6.98; Cl, 17.30.

Example 57

Dimethyl 2-[4-(8-benzyl-8-azabicyclo[3.2.1]octan-3-yl)-1-piperazinyl]carbonylmethyl-4-(2,6-dichlorophenyl)-6-[2-(2-methoxyphenyl)ethyl]-1,4-dihydropyridine-3,5-dicarboxylate This was prepared according to the procedure of Example 10, as HCl salt, mp 178°–181° C.

$^1$H NMR (free base, CDCl$_3$) δ 1.40–1.75 (m, 7H), 1.90–2.10 (m, 2H), 2.35–2.65 (m, 4H), 2.75–3.00 (m, 4H), 3.25 (br. s, 2H), 3.54 (s, 3H), 3.55 (s, 3H), 3.50–3.70 (m, 7H), 3.92 (s, 3H), 4.27 (d, J=15.0 Hz, 1H), 5.98 (s, 1H), 6.80–6.90 (m, 2H), 6.98 (t, J=7.92 Hz, 1H), 7.15–7.45 (m, 9H), 7.92 (s, 1H). IR (KBr): 3420, 2950, 1690, 1650 cm$^{-1}$. Anal. Calcd for C$_{40}$H$_{50}$Cl$_2$N$_4$O$_6$.2HCl.H$_2$O: C, 59.20; H, 6.10; N, 6.28; Cl, 15.88. Found: C, 58.85; H, 6.59; N, 6.05; Cl, 16.06.

Example 58

Dimethyl 2-[4-(bicyclo[3.3.0]octan-3-one-7-yl)-1-piperazinyl]carbonylmetnyl-4-(2,6-dichlorophenyl)-6-[2-(2-methoxyphenyl)ethyl]-1,4-dihydropyridine-3,5-dicarboxylate This was prepared according to the procedure of Example 2, as HCl salt, mp 145°–150° C.

$^1$H NMR (free base, CDCl$_3$) δ 1.25–1.45 (m, 2H), 2.05–2.30 (m, 3H), 2.35–2.80 (m, 10H), 2.80–3.00 (m, 4H), 3.54 (s, 3H), 3.56 (s, 3H), 3.55–3.75 (m, 5H), 3.92 (s, 3H), 4.27 (d, J=15.0 Hz, 1H), 5.99 (s, 1H), 6.80–6.90 (m, 2H), 7.00 (t, J=7.9 Hz, 1H), 7.10–7.30 (m, 4H), 7.85 (s, 1H). IR (KBr): 3450, 2950, 1735, 1690, 1650 cm$^{-1}$. Anal. Calcd for C$_{38}$H$_{43}$Cl$_2$N$_3$O$_7$.HCl.H$_2$O: C, 58.67; H, 5.96; N, 5.40. Found: C, 58.35; H, 6.27; N, 5.15.

Example 59

Dimethyl 2-[4-(bicyclo[3.3.0]octan-3-ol-7-yl)-1-piperazinyl]carbonylmethyl-4-(2,6-dichlorophenyl)-6-[2-(2-methoxyphenyl)ethyl]-1,4-dihydropyridine-3,5-dicarboxylate This was prepared according to the procedure of Example 3, as HCl salt, mp 155°–160° C.

$^1$H NMR (free base, CDCl$_3$) δ 1.45–1.60 (m, 2H), 1.60–1.95 (m, 4H), 2.00–2.20 (m, 4H), 2.25–2.60 (m, 6H), 2.75–3.00 (m, 4H), 3.54 (s, 3H), 3.55 (s, 3H), 3.50–3.75 (m, 5H), 3.92 (s, 3H), 4.15–4.40 (m, 2H), 5.98 (s, 1H), 6.80–6.90 (m, 2H), 7.00 (t, J=7.7 Hz, 1H), 7.15–7.30 (m, 4H), 7.79 (s, 1H). IR (KBr): 3400, 2950, 1690, 1650 cm$^{-1}$. Anal. Calcd for C$_{38}$H$_{45}$Cl$_2$N$_3$O$_7$.HCl.H$_2$O: C, 58.52; H, 6.21; N, 5.39. Found: C, 58.21; H, 6.48; N, 5.34.

Example 60

Dimethyl 2-[4-(bicyclo[3.3.0]octan-3-amine-7-yl)-1-piperazinyl]carbonylmethyl-4-(2,6-dichlorophenyl)-6-[2-(2-methoxyphenyl)ethyl]-1,4-dihydropyridine-3,5-dicarboxylate This was prepared according to the procedure of Example 4, as HCl salt. Isomer A: mp 189.5°–191° C. (dec).

$^1$H NMR (free base, CDCl$_3$) δ 1.00–1.20 (m, 4H), 1.75–1.95 (m, 4H), 2.10–2.25 (m, 2H), 2.30–2.50 (m, 4H), 2.55–2.70 (m, 2H), 2.75–3.00 (m, 5H), 3.54 (s, 3H), 3.50–3.75 (m, 5H), 3.92 (s, 3H), 4.26 (d, J=15.0 Hz, 1H), 5.98 (s, 1H), 6.75–6.95 (m, 2H), 7.00 (t, J=7.7 Hz, 1H), 7.15–7.35 (m, 4H), 7.87 (s, 1H). IR (KBr): 3450, 2950, 1690 cm$^{-1}$. Anal. Calcd for $C_{38}H_{46}Cl_2N_4O_6 \cdot 2HCl \cdot H_2O$: C, 55.89; H, 6.17; N, 6.86; Cl, 17.36. Found: C, 55.77; H, 6.42; N, 6.78; Cl, 17.74. Isomer B: mp 194.5°–195.5° C. (dec);

$^1$H NMR (free base, CDCl$_3$) δ 0.80–1.30 (m, 4H), 1.50–1.80 (m, 2H), 2.05–2.25 (m, 4H), 2.36–2.60 (m, 6H), 2.70–3.00 (m, 4H), 3.25 (m, 1H), 3.54 (s, 3H), 3.55 (s, 3H), 3.60–3.75 (m, 6H), 3.92 (s, 3H), 4.26 (d, J=15.0 Hz, 1H), 5.98 (s, 1H), 6.80–6.95 (m, 2H), 6.99 (t, J=8.4 Hz, 1H), 7.15–7.35 (m, 4H), 7.91 (br. s, 1H). IR (KBr): 3450, 2950, 1690 cm$^{-1}$. Anal. Calcd for $C_{38}H_{46}Cl_2N_4O_6 \cdot 2HCl \cdot H_2O$: C, 55.89; H, 6.17; N, 6.86; Cl, 17.36. Found: C, 55.95; H, 6.43; N, 6.70; Cl, 17.23.

Example 61

Dimethyl 4-(2,6-dichlorophenyl)-2-(4-methyl-1-piperazinyl)carbonylmethyl-6-phenacyl-1,4-dihydropyridine-3,5dicarboxylate A. Methyl 5-(1,3-dioxolan-2-yl)-3-oxo-5-phenylpentanoate To a stirred solution of 3-(1,3-dioxolan-2-yl)-3-phenylpropionic acid (prepared according to Yamaguchi's procedure: *J. Chem. Soc. Chem. Commun.*, 1988, 27; 23.68 g, 114 mmol) and Meldrum's acid (13.69 g, 95 mmol) in THF (200 ml) was added diethyl phosphorocyanidate (18.3 ml, 114 mmol) and trietylamine (40 ml, 287 mmol) dropwise at 0° C. The reaction mixture was stirred at 0° C. for 2 h and at ambient temperature for 16 h. The solvent was evaporated and 5% NaHCO$_3$ aqueous solution was added to the residue. The aqueous solution was washed with ethyl acetate. The aqueous layer was then acidified with c-HCl and extracted with ethyl acetate. The extract combined was washed with brine and dried (MgSO$_4$). Evaporation of the solvent afforded 14.05 g of brown color oil solid mixture which was washed with methanol to give 5.92 g of white solid. The organic layer was dried (MgSO$_4$) and concentrated to give 34.40 g of brown viscous oil. Methanol was added to this oil to form solid, which was collected by filtration and washed with methanol to afford 5.51 g of pale yellow solid. Total 11.43 g (36%) of Meldrum's acid derivative was obtained. This was refluxed in methanol (40 ml) for 4 h. The solvent was evaporated to give yellow viscous oil which was purified by column chromatography on silica gel (hexane/ethyl acetate: 4/1 as eluent) to afford 7.69 g (85.1%)of title compound as pale yellow clear oil.

$^1$H NMR (CDCl$_3$) δ 2.82 (s, 0.2H), 3.13 (s, 2H), 3.58 (s, 2H), 3.70 (s, 0.3H), 3.72 (s, 3H), 3.76–3.86 (m, 2.2H), 4.00–4.09 (m, 2.2H), 5.02 (s, 0.1H), 7.31–7.39 (m, 3.3H), 7.46–7.49 (m, 2.2H), 11.96 (br. s, 0.1H). IR (neat): 3659, 3550, 1740, 1715, 1650, 1630 cm$^{-1}$. Anal. Calcd for $C_{14}H_{16}O_5$: C, 63.62; H, 6.10. Found: C, 63.17; H, 6.16.

B. Dimethyl 4-(2,6-dichlorophenyl)-6-[2-(1,3-dioxolan-2-yl)-2-phenylethyl]-2-methoxycarbonylmethyl-1,4-dihydropyridine-3,5-dicarboxylate This was prepared by a procedure similar to that described in Example 15, as pale yellow solid, mp 56°–57° C.

$^1$H NMR (CDCl$_3$) δ 3.30 (d, J=15.4 Hz, 1H), 3.49 (s, 3H), 3.52 (s, 3H), 3.68 (d, J=16.5 Hz, 1H), 3.76 (s, 3H), 3.76 (d, J=14.8 Hz, 1H), 3.85 (d, J=15.8 Hz, 1H), 3.70–3.87 (m, 2H), 4.08–4.17 (m, 2H), 5.98 (s, 1H), 6.97 (dd, J=7.3, 8.1 Hz, 1H), 7.22 (d, J=8.1 Hz, 2H), 7.27–7.38 (m, 3H), 7.51 (dd, J=1.8, 8.1 Hz, 2H), 7.62 (br. s, 1H). IR (nujol): 3340, 1745, 1700, 1660, 1650, 1630 cm$^{-1}$. Anal. Calcd for $C_{28}H_{27}Cl_2NO_8$: C, 58.34; H, 4.72; N, 2.43. Found: C, 57.92; H, 4.73; N, 2.45.

C. Dimethyl 4-(2,6-dichlorophenyl)-2-(4-methyl-1-tpiperazinyl)carbonylmethyl-6-phenacyl-1,4-dihydropyridine-3,5-dicarboxylate A mixture of the above triester derivative (0.67 g, 1.16 mmol), 6N NaOH aqueous solution (0.3 ml, 1.8 mmol), and methanol (2 ml) was stirred at room temperature for 0.5 h. The reaction mixture was diluted with water (10 ml), washed with ethyl acetate. Then the aqueous solution was acidified with 1N HCl and extracted with dichloromethane. The extracts combined was dried (MgSO$_4$) and concentrated to give 0.47 g of brown solid. To a stirred solution of this solid (0.47 g) in dichloromethane (20 ml) was added N-methylpiperazine (0.15 g, 1.5 mmol) and 1-ethyl-3-(3-dimethyl-aminopropyl)carbodiimide hydrochloride (0.29 g, 1.5 mmol) at room temperature and the reaction mixture was stirred at room temperature for 1 h. The reaction mixture was washed with water and brine, and dried (MgSO$_4$). Evaporation of the solvent afforded 441 mg of brown color viscous oil which was purified by preparative thin layer chromatography (Rf=0.34, developed with dichloromethan/methanol: 10/1) to give 407 mg (74.8%) of pale yellow crystalline. A mixture of this crystalline, 1N HCl (2 ml) and acetone (8 ml) was stirred at 60° C. for 2.5 h. The reaction mixture was diluted with ethyl acetate (20 ml), basified with NaHCO$_3$ aqueous solution and extracted with ethyl acetate. The extracts combined was dried (MgSO$_4$) and concentrated to give 266 mg of orange color amorphous solid. This was purified by preparative thin layer chromatography (Rf=0.32, developed twice with dichloromethane/methanol: 10/1) to give 201 mg (53%) of yellow viscous oil. This oil was treated with HCl saturated methanol (10 m) and concentrated to give yellow solid, which was crystallized from methanol/ether to afford 110 mg of pale yellow powder, mp 207°–209°.

$^1$H NMR (free base, CDCl$_3$) δ 2.31 (s, 3H), 2.32–2.50 (m, 4H), 3.45 (s, 3H), 3.55 (s, 3H), 3.59–3.75 (m, 4H), 3.83 (d, J=15.4 Hz, 1H), 4.07 (d, J=16.5 Hz, 1H), 4.23 (br. d, J=17.2 Hz, 1H), 4.79 (br. d, J=16.5 Hz, 1H), 6.06 (s, 1H), 7.00 (dd, J=7.7, 8.1 Hz, 1H), 7.24 (d, J=8.8 Hz, 2H), 7.41–7.57 (m, 3H), 8.02 (d, J=7.3 Hz, 2H), 8.34 (br. s, 1H), IR (nujol): 3650, 3450, 3210, 3100, 1695, 1675, 1655, 1635 cm$^{-1}$. Anal. Calcd for $C_{30}H_{31}Cl_2N_2O_6 \cdot HCl \cdot 1.5H_2O$: C, 54.27; H, 5.31; N, 6.33; Cl, 16.02. Found: C, 54.44; H, 5.28; N, 6.43; Cl, 15.82.

Example 62

Dimethyl 4-(2,6-dichlorophenyl)-2-[4-(3-dimethylaminopropyl)-1-piperazinyl]carbonylmethyl-6-[2-(2-methoxyphenyl)ethyl]-1,4-dihydropyridine-3,5-dicarboxylate A. 4-Benzyloxycarbonyl-3-dimethylaminopropylpiperazine A suspension mixture of benzyloxycarbonylpiperazine (14.529, 65.9 mmol), 3-dimethyl-aminopropyl chloride hydrochloride (15.63 g, 98.9 mmol), and triethylamine (20.29, 200 mmol) in ethanol (100 ml) was refluxed for 14 h. Then 3-dimethylaminopropyl chloride hydrochloride (6.32 g, 40 mmol), and triethylamine (11.3 ml, 80 mmol) was added to the reaction mixture and continued to reflux for 24 h. The solvent was evaporated and the residue was extracted with ethyl actate. The extract was washed with water, dried (MgSO$_4$), and concentrated to give 12.65 g of brown viscous oil, which was purified by column chromatography on silica gel (ammonium hydroxide aqueous solution/methanol/dichloromethane: 1/10/100) to give 2.21 g of brown clear oil.

$^1$H NMR (CDCl$_3$) δ 1.60–1.72 (m, 2H), 2.22 (s, 6H), 2.27–2.45 (m, 8H), 3.52 (t, J=5.1 Hz, 4H), 5.13 (s, 2H), 7.27–7.37 (m, 5H). IR (neat): 1700 cm$^{-1}$.

B. 3-Dimethylaminopropylpiperazine

A mixture of 4-benzyloxycarbonyl-3-dimethylaminopropylpiperazine (2.21 g, 7.2 mmol), 5% Pd/C (0.36 g) in methanol (20 ml) was stirred under hydrogen atmosphere at room temperature for 38 h. After removal of catalyst by Celite filtration, the filtrate was concentrated to afford 1.20 g (97.6%) of orange color viscous oil.

$^1$H NMR (CDCl$_3$) δ 1.61–1.73 (m, 2H), 2.01 (br.s, 1H), 2.22 (s, 6H), 2.26–2.45 (m, 8H), 2.90 (br.t, J=4.8 Hz, 4H). IR (neat): 3270 cm$^{-1}$.

C. Dimethyl 4-(2,6-dichlorophenyl)-2-[4-(3-dimethylaminopropyl)-1-piperazinyl]carbonylmethyl-6-[2-(2-methoxyphenyl)ethyl]-1,4-dihydropyridine-3,5-dicarboxylate This was prepared by a procedure similar to that described in Example 6, as HCl salt, mp 156°–158° C.

$^1$H NMR (free base, CDCl$_3$) δ 1.65–1.80 (m, 2H), 2.36 (s, 6H), 2.30–2.55 (m, 10H), 2.80–3.00 (m, 2H), 3.54 (s, 3H), 3.55 (s, 3H), 3.60–3.70 (m, 5H), 3.92 (s, 3H), 4.25 (d, J=15.0 Hz, 1H), 5.98 (s, 1H), 6.84–6.89 (m, 2H), 6.99 (dd, J=7.3, 8.4 Hz, 1H), 7.16–7.27 (m, 4H), 7.89 (br. s, 1H). IR (neat): 3370, 3270, 3200, 1690, 1645, 1630 cm$^{-1}$. Anal. Calcd for C$_{35}$H$_{44}$Cl$_2$N$_4$O$_6$.2HCl.3H$_2$O: C, 51.60; H, 6.43; N, 6.88; Cl, 17.41. Found: C, 51.46; H, 6.80; N, 6.81; Cl, 17.79.

Some intermediate compounds were prepared in the following manner.

Preparation 1
Dimethyl 4-(2,6-dichlorophenyl)-2-methoxycarbonylmethyl-6-(2-phenylethyl)-1,4-dihydropyridine-3,5-dicarboxylyate A. Dimethyl 2-amino-1-propene-1,3-dicarboxylate To a stirred solution of dimethyl acetonedicarboxylate (44.1 ml, 0.3 mole) and p-toluene-sulfonic acid (0.19 g, 1 mmol) in benzene (50 ml) was bubbled NH$_3$ gas for 30 min. The mixture was refluxed with azeotropic removal of water using Dean-Stark trap. The bubbling of NH$_3$ gas and azeotropic removal of water was repeated three times to give a total 5 ml of water. The reaction mixture was diluted with benzene and filtered through celite. The filtrate was concentrated to give an amber oil, 50.75 g. An equal volume of ether was added to this oil and hexane added until cloudy, and stirred slowly overnight to afford a crystalline product. This crystalline was collected by filtration and washed once with 1/1 of ether/hexane to give 44.55 g (85.75%) of crystalline, mp 47°–50° C.

$^1$H NMR (CDCl$_3$) δ 3.16 (s, 2H), 3.64 (s, 3H), 3.73 (s, 3H), 4.58 (s, 1H).

B. Methyl 2-(2,6-dichlorophenylmethylidene)-3-oxo-5-phenylpentanoate

A mixture of methyl 3-oxo-5-phenylpentanoate (10 g, 48.5 mmol), 2,6-dichlorobenzaldehyde (8.486 g, 48.5 mmol), acetic acid (0.56 ml, 9.7 mmol), and piperidine (0.24 ml, 2.42 mmol) in benzene (100 ml) was refluxed with azeotropic removal of water for 3 h. After cooled down, the reaction mixture was wash with water, NaHCO$_3$ aqueous solution, and brine, and dried over Na$_2$SO$_4$. Evaporation of the solvent afforded crude viscous oil, which was used for next reaction without purification. $^1$H NMR data indicated that this was 1:1 mixture of E and Z isomers.

$^1$H NMR (CDCl$_3$) δ 2.83–3.14 (m, 4H), 3.59 and 3.83 (each s, total 3H), 7.20 (m, 8H), 7.56 and 7.60 (each s, total 1H).

C. Dimethyl 4-(2,6-dichlorophenyl)-2-methoxycarbonylmethyl-6-[2-(phenyl)ethyl]-1,4-dihydropyridine-3,5-dicarboxylate A mixture of methyl 2-(2,6-dichlorophenylmethylidene)-3-oxo-5-phenylpentanoate(the crude product from the preceding experiment) and dimethyl 2-amino-1-propene-1,3-dicarboxylate (8.4 g, 48.5 mmol) was heated without solvent at 120° C. for 18 h. TLC showed a strong fluorescent spot at Rf=0.3 (dichloromethane/ethyl acetate: 24/1). This reaction mixture was chromatographed on 1.5 kg silica gel to yield 3.93 g of product. An additional 2 g of slightly impure product was also obtained.

$^1$H NMR (CDCl$_3$) δ 2.91 (m, 4H), 3.52 (s, 3H), 3.58 (s, 3H), 3.68 (ABq, J=17 Hz, 2H), 3.70 (s, 3H), 5.98 (s, 1H), 6.93 (br. s, 1H), 6.99 (t, J=8.57 Hz, 1H), 7.23 (m, 7H).

Preparation 2
Dimethyl 6-[(2-benzylthio)ethyl]-4-(2,6-dichlorophenyl)-1,4-dihydropyridine-3,5-dicarboxylate A mixture of dimethyl 2-amino-1-propene-1,3-dicarboxylate(4.8 g, 27.7 mmole), 2,6-dichlorobenzaldehyde (4.85 g, 27.7 mmole), and methyl 5-benzylthio-3-oxo-pentanoate (7.0 g, 27.7 mmole) in methanol was refluxed for one week. Daily monitoring by TLC showed increasing amounts of the blue fluorescent product at Rf=0.55. The solvent was evaporated and the residue was chromatographed on 1.32 kg of silica gel (dichloromethane/ethyl acetate: 24/1 as eluent) to afford 2.794 g of title compound.

$^1$H NMR (CDCl$_3$) δ 2.69 (m, 3H), 2.96 (m, 1H), 3.5 (s, 3H), 3.55 (s, 3H), 3.72 (s, 3H), 3.74 (AB$_q$, J=15.6 Hz, 2H), 3.78 (s, 2H), 5.92 (s, 1H), 6.86 (br. s, 1H), 6.65 (t, 1H), 7.27, (m, 7H).

Preparation 3
5-t-Butoxycarbonyl-4-(2,6-dichlorophenyl)-3-methoxycarbonyl-2-methoxycarbonylmethyl-6-methyl-1,4-dihydropyridine A mixture of t-butyl 3-amino-2-butenoate (3.911 g, 24.8 mmol), 2,6-dichlorobenzaldehyde (4.354 g, 24.8 mmol), and dimethyl acetonedicarboxylate (3.657 ml, 24.8 mmol) in methanol (50 ml) was refluxed for 45 h. The solvent was evaporated and the residue was chromatographed on 800 g silica gel (dichloromethane/ethyl acetate: 23/2 as eluent) to give 1.18 g of product. On silica GF plates, the product was blue fluorescent at Rf=0.3.

$^1$H NMR (CDCl$_3$) δ 1.29 (s, 9H), 2.07 (s, 3H), 3.5 (s, 3H), 3.72 (s, 3H), 3.76 (AB$_q$, J=16.9 Hz, 2H), 5.90 (s, 1H), 6.58 (br. s, 1H), 6.97 (dd, 1H), 7.22 (d, 2H).

Preparation 4
Dimethyl 4-(2,6-dichlorophenyl)-2-methoxycarbonylmethyl-6-[2-(2-methoxyphenyl)ethyl]-1,4-dihydropyridine-3,5-dicarboxylate A. 2,2-Dimethyl-5-[3-(2-methoxythenyl)propanoyl]-1,3-dioxane-4,6-dione To a stirred solution of Meldrum's acid (16.609, 0.115 mol) in dichloromethane (50 ml) was added pyridine (18.2 g, 0.23 mol) followed by dropwise addition of solution of 3-(2-methoxyphenyl)propionyl chloride (27.5 g, 0.138 mol) in dichloromethane (30 ml) at 0° C. The reaction mixture was stirred at 0° C. to room temperature overnight. The reaction mixture was diluted with dichloromethane (100 ml), washed with 1N HCl and brine, and dried (MgSO$_4$). Evaporation of the solvent gave 29.5 g(83.7%) of solid.

$^1$H NMR (CDCl$_3$) δ 1.65 (s, 6H), 2.60–3.00 (m, 2H), 3.40 (t, 2H), 3.80 (s, 3H), 6.80–7.25 (m, 4H).

B. Methyl 5-(2-methoxyphenyl)-3-oxobutanoate

A mixture of 2,2-dimethyl-5-[3-(2-methoxyphenyl)propanoyl]-1,3-dioxane-4,6-dione (29 g, 94.7 m mol) and methanol (70 ml) was refluxed for 3 h. The solvent was evaporated and the residue was extracted with ethyl actate. The extract was washed with NaHCO$_3$ aqueous solution and brine, dried (MgSO$_4$), and concentrated to afford 22.3 g(100%) of desired compound as an oil.

$^1$H NMR (CDCl$_3$) δ 2.60–3.00 (m, 4H), 3.40 (s, 2H), 3.70 (s, 3H), 3.80 (s, 3H), 4.4 (s, 2H), 6.80–7.30 (m 4H).

C. Dimethyl 4-(2,6-dichlorophenyl)-2-methoxycarbonylmethyl-6-[2-(2-methoxyphenyl)ethyl]-1,4-dihydropyridine-3,5-dicarboxylate This was prepared by a procedure similar to that described in Example 15, mp 183°–184° C.

$^1$H NMR (CDCl$_3$) δ 2.86–2.93 (m, 4H), 3.53 (s, 3H), 3.55 (s, 3H), 3.70 (d, J=16.9 Hz, 1H), 3.74 (s, 3H), 3.77 (d, J=16.5 Hz, 1H), 3.90 (s, 3H), 5.99 (s, 1H), 6.86–6.92 (m, 3H), 6.98 (dd, J=7.7, 8.4 Hz, 1H), 7.17–7.22 (m, 4H). IR (nujol): 3350, 1740, 1695, 1680, 1650, 1630 cm$^{-1}$. Anal. Calcd for C$_{27}$H$_{27}$Cl$_2$NO$_7$: C, 59.13; H, 4.96; N, 2.55; Cl, 12.93. Found: C, 58.83; H, 5.01; N, 2.47; Cl, 12.58.

We claim:

1. A compound of the formula:

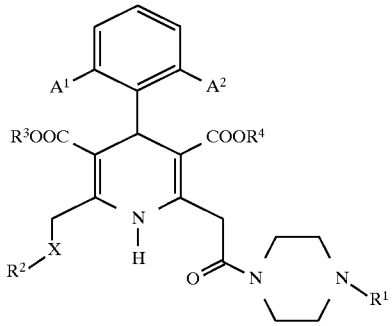

and its pharmaceutically acceptable salts, wherein

A$^1$ and A$^2$ are each halo;

X is a direct bond, CH$_2$, CO, O, S, S(O) or S(O)$_2$;

R$^1$ is selected from the following:
(a) hydrogen, C$_{1-4}$ alkyl optionally substituted with one or two substituents selected from hydroxy, amino, C$_{1-4}$ alkylamino, di-C$_{1-4}$ alkylamino, pyridyl, carbamoyl, pyrrolidinocarbonyl, propylaminocarbonyl, piperidinocarbonyl or morpholinocarbonyl;
(b) piperidinyl optionally substituted on the nitrogen atom with C$_{1-4}$ alkyl or C$_{1-4}$ alkoxycarbonyl;
(c) C$_{5-14}$ cycloalkyl, bicycloalkyl or tricycloalkyl, optionally substituted with one or two substituents selected from oxo, hydroxy, amino, C$_{1-4}$ alkylamino, di-C$_{1-4}$ alkylamino, methoxybenzamido or morpholino;
(d) C$_{7-14}$ azacyclo-, azabicyclo- or azatricyclo-alkyl, in which the nitrogen atom optionally has a substituent selected from C$_{1-4}$ alkyl, benzyl optionally substituted with one or two substituents selected from halo and trihalo C$_{1-4}$ alkyl, C$_{1-4}$ alkyloxycarbonyl optionally substituted with one or two halogen atoms and C$_{2-5}$ acyl; and
(e) C$_{7-10}$ bicycloalkenyl, benzo C$_{5-7}$ cycloalkyl or heterocyclic selected from a monocyclic or bicyclic hydrocarbon group having 4 to 10 carbon atoms and 1 to 3 hetero atoms;

R$^2$ is hydrogen, C$_{1-4}$ alkyl, phenyl optionally substituted with one or two substituents selected from halo, C$_{1-4}$ alkyl, trihalo C$_{1-4}$ alkyl and C$_{1-4}$ alkoxy, or heterocyclic selected from a monocyclic or bicyclic hydrocarbon group having 4 to 10 carbon atoms and 1 to 3 hetero atoms; selected from a monocyclic or bicyclic hydrocarbon group having 4 to 10 carbon atoms and 1 to 3 hetero atoms; and R$^3$ and R$^4$ are each C$_{1-3}$ alkyl.

2. A compound according to claim 1, wherein A$^1$ and A$^2$ are each chloro or bromo; R$^1$ is selected from group (a); R$^2$ is hydrogen, C$_{1-4}$ alkyl or phenyl optionally substituted with one or two substituents selected from halo, C$_{1-4}$ alkyl, trihalo C$_{1-4}$ alkyl and C$_{1-4}$ alkoxy; and R$^3$ and R$^4$ are each C$_{1-3}$ alkyl.

3. A compound according to claim 2, wherein X is a direct bond or CH$_2$; R$^1$ is hydrogen, pyridylmethyl, pyrrolidinylcarbonyl, propylaminocarbonyl, hydroxyethyl or dimethylaminopropyl; R$^2$ is hydrogen, phenyl, methoxyphenyl, propyl(methoxy)phenyl, methylphenyl, chlorophenyl, pyridyl or thienyl; and R$^3$ and R$^4$ are both methyl.

4. A compound according to claim 1, wherein A$^1$ and A$^2$ are each chloro or bromo; X is a direct bond or —CH$_2$—; R$^1$ is selected from group (b); R$^2$ is hydrogen, C$_{1-4}$ alkyl or phenyl optionally substituted with one or two substituents selected from halo, C$_{1-4}$ alkyl, trihalo C$_{1-4}$ alkyl and C$_{1-4}$ alkoxy; and R$^3$ and R$^4$ are each C$_{1-3}$ alkyl.

5. A compound according to claim 4, wherein R$^1$ is piperidinyl, 1-(butylcarbonyl)piperidinyl or 1-methylpiperidinyl; and R$^2$ is hydrogen, phenyl, methoxyphenyl, propyl(methoxy)phenyl, methylphenyl, chlorophenyl, pyridinyl or thienyl; and R$^3$ and R$^4$ are both methyl.

6. A compound according to claim 1, wherein A$^1$ and A$^2$ are each chloro or bromo; X is a direct bond or —CH$_2$—; R$^1$ is selected from group (c); R$^2$ is hydrogen, C$_{1-4}$ alkyl or phenyl optionally substituted with one or two substituents selected from halo, C$_{1-4}$ alkyl, trihalo C$_{1-4}$ alkyl and C$_{1-4}$ alkoxy; and R$^3$ and R$^4$ are each C$_{1-3}$ alkyl.

7. A compound according to claim 6, wherein R$^1$ is C$_{5-6}$ cycloalkyl, bicyclo[3.2.1]octyl or one of the following:

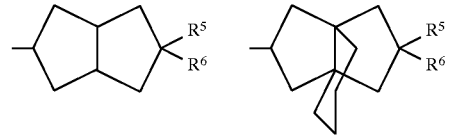

(wherein R$^5$ is hydrogen and R$^6$ is hydroxy, amino, methoxybenzamido or morpholino, or R$^5$ and R$^6$ are taken together to represent an oxo group);

R$^2$ is hydrogen, phenyl, methoxyphenyl, propyl(methoxy)phenyl, methylphenyl, chlorophenyl, pyridinyl or thienyl; and R$^3$ and R$^4$ are both methyl.

8. A compound according to claim 1, wherein

A$^1$ and A$^2$ are each chloro or bromo; X is a direct bond or —CH$_2$—; R$^1$ is selected from group (d); R$^2$ is hydrogen, C$_{1-4}$ alkyl or phenyl optionally substituted with one or two substituents selected from halo, C$_{1-4}$ alkyl, trihalo C$_{1-4}$ alkyl and C$_{1-4}$ alkoxy; and R$^3$ and R$^4$ are each C$_{1-3}$ alkyl.

9. A compound according to claim 8, wherein R$^1$ is selected from the following groups:

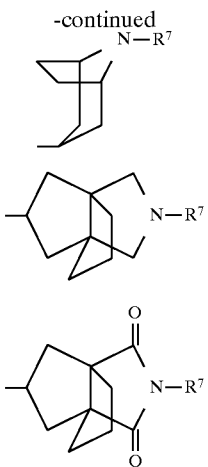

(wherein $R^7$ is hydrogen, $C_{1-4}$ alkyl, benzyl optionally substituted with one or two substituents selected from halo and trihaloalkyl, acetyl or chloroethoxycarbonyl);

$R^2$ is hydrogen, phenyl, methoxyphenyl, propyl(methoxy) phenyl, methylphenyl, chlorophenyl, pyridinyl or thienyl; and $R^3$ and $R^4$ are both methyl.

10. A compound according to claim 1, wherein $A^1$ and $A^2$ are each chloro or bromo; X is a direct bond or —$CH_2$—; $R^1$ is selected from group (e); $R^2$ is hydrogen, $C_{1-4}$ alkyl or phenyl optionally substituted with one or two substituents selected from halo, $C_{1-4}$ alkyl, trihalo $C_{1-4}$ alkyl and $C_{1-4}$ alkoxy; and $R^3$ and $R^4$ are each $C_{1-3}$ alkyl.

11. A compound according to claim 10, wherein $R^1$ is norbornenyl, indanonyl, quinuclidinyl or pyrimidinyl; $R^2$ is hydrogen, phenyl, methoxyphenyl, propyl(methoxy)phenyl, methylphenyl, chlorophenyl, pyridinyl or thienyl; and $R^3$ and $R^4$ are both methyl.

12. A compound according to claim 1, being one of the following:

dimethyl4-(2,6-dichlorophenyl)-2-(4-methyl-1-piperazinyl) carbonylmethyl-6-phenylsulfinylmethyl-1,4-dihydropyridine-3,5-dicarboxylate;

dimethyl 4-(2,6-dichlorophenyl)-6-[2-(2-methoxyphenyl) ethyl]-2-[4-(8-methyl-8-azabicyclo[3.2.1]octan-3-yl)-1-piperazinyl]carbonylmethyl-1,4-dihydropyridine-3,5-dicarboxylate; and dimethyl 4-(2,6-dichlorophenyl)-6-[2-(2-methoxyphenyl) ethyl]-2-[4-( 3-quinuclidinyl)-1-piperazinyl] carbonylmethyl-1,4-dihydropyridine-3,5-dicarboxylate.

13. A pharmaceutical composition for the treatment of inflammation, cardiovascular disease, pain, common cold, allergies, asthma, pancreatitis, burns, virus infection, head injury, multiple trauma or the like, which comprises a therapeutically effective amount of a compound of claim 1 or its pharmaceutically acceptable carrier.

* * * * *